United States Patent
Oh et al.

(10) Patent No.: US 10,182,980 B2
(45) Date of Patent: Jan. 22, 2019

(54) METHOD OF MAKING AN AMINO SILICONE NANOEMULSION

(71) Applicant: The Procter & Gamble Company, Cincinnati, OH (US)

(72) Inventors: Hiroshi Oh, Cincinnati, OH (US); Steven Daryl Smith, Fairfield, OH (US); Vladimir Gartstein, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 88 days.

(21) Appl. No.: 15/005,107

(22) Filed: Jan. 25, 2016

(65) Prior Publication Data

US 2016/0213598 A1     Jul. 28, 2016

(51) Int. Cl.
| | |
|---|---|
| A61K 8/06 | (2006.01) |
| A61K 8/891 | (2006.01) |
| A61Q 13/00 | (2006.01) |
| A61Q 5/00 | (2006.01) |
| A61Q 5/02 | (2006.01) |
| A61Q 5/12 | (2006.01) |
| A61Q 5/06 | (2006.01) |
| C11D 3/37 | (2006.01) |
| A61Q 19/10 | (2006.01) |
| A61K 8/898 | (2006.01) |
| B01F 17/54 | (2006.01) |
| C08J 3/03 | (2006.01) |

(52) U.S. Cl.
CPC ............. *A61K 8/891* (2013.01); *A61K 8/06* (2013.01); *A61K 8/898* (2013.01); *A61Q 5/002* (2013.01); *A61Q 5/02* (2013.01); *A61Q 5/06* (2013.01); *A61Q 5/12* (2013.01); *A61Q 13/00* (2013.01); *A61Q 19/10* (2013.01); *B01F 17/0071* (2013.01); *C08J 3/03* (2013.01); *C11D 3/3742* (2013.01); *A61K 2800/21* (2013.01); *A61K 2800/34* (2013.01); *A61K 2800/49* (2013.01); *A61K 2800/592* (2013.01); *A61K 2800/95* (2013.01); *C08J 2383/08* (2013.01)

(58) Field of Classification Search
CPC .................................. A61K 8/891; A61K 8/06
See application file for complete search history.

(56) References Cited

U.S. PATENT DOCUMENTS

| | | |
|---|---|---|
| 4,541,936 A | 9/1985 | Ona et al. |
| 5,244,598 A | 9/1993 | Merrifield et al. |
| 5,712,343 A | 1/1998 | Geck et al. |
| 5,925,341 A | 7/1999 | Cervantes et al. |
| 6,177,511 B1 | 1/2001 | Dauth et al. |
| 2006/0263611 A1 | 11/2006 | Weberg et al. |
| 2006/0269506 A1 | 11/2006 | Decaire et al. |
| 2007/0042124 A1 | 2/2007 | Kazuyuki et al. |
| 2011/0159301 A1 | 6/2011 | Wakamatsu et al. |
| 2012/0321679 A1 | 12/2012 | Yoshitsugu et al. |

FOREIGN PATENT DOCUMENTS

| | | |
|---|---|---|
| CN | 102031698 A | 4/2011 |
| EP | 0972789 A1 | 1/2000 |
| WO | WO 2004092475 A1 | 10/2004 |
| WO | WO 2008142998 A1 | 11/2008 |
| WO | WO 2009033399 A1 | 3/2009 |

OTHER PUBLICATIONS

International Search Report and Written Opinion dated Mar. 31, 2016, 12 pgs.
International Search Report and Written Opinion dated Apr. 15, 2016, 13 pgs.

*Primary Examiner* — Alma Pipic
(74) *Attorney, Agent, or Firm* — Jason J Camp

(57) ABSTRACT

The present invention relates to a method of making an amino silicone nanoemulsions. More specifically, the present invention relates to a method of making an amino silicone nanoemulsions that may be used to protect surfaces from being soiled or wetted.

8 Claims, No Drawings

METHOD OF MAKING AN AMINO SILICONE NANOEMULSION

FIELD OF THE INVENTION

The present invention relates to a method of making an amino silicone nanoemulsion. More specifically, the present invention relates to a method of making an amino silicone nanoemulsion that may be used to protect surfaces from being soiled or wetted.

BACKGROUND OF THE INVENTION

Numerous attempts have been made to develop a treatment composition that provides protection of surfaces by repelling water and oil based soils from the surface. Fluoropolymers, such as those used in Scotchguard® from 3M, have become well established as soil-repellant molecules. However, fluoropolymers are not preferred due to environmental, and health and safety concerns, such as potential and possibility of persistent bioaccumulation and toxicity.

The combination of polyorganosiloxane fluids and silicone resins in attempts to treat hard or soft surfaces is also known. Silicone resins are highly cross-linked silicone materials that have very high viscosities. These materials are generally difficult to handle in a manufacturing environment and difficult to formulate with, given their high viscosities. And, incorporating compositions containing silicone resins into liquid-based and emulsion-based treatment formulations generally requires high energy processes.

Silicone lattices, where crosslinking in emulsion occurs by means of a condensation reaction, addition reaction, or free-radical polymerization reaction, are known. Self-crosslinking silicone emulsions, where crosslinking occurs via acetoxy, aminoxy, acetamido, carboxyl, cycloalkyl, or oxime groups, are known. And, emulsions and microemulsions of amino-functional organosiloxanes and di- and/or oligo(meth)acrylates, and their Michael addition products are also known.

Unfortunately, to date, the attempts at non-fluoropolymer protection of surfaces continue to demonstrate disadvantages, including low efficiency, difficulty in achieving the desired benefits at affordable cost and in a preferred format, processing and formulation challenges, and product instability. A continued need exists for a non-fluoropolymer technology that delivers depositable benefits to surfaces, such as water and oily soil repellency, in a convenient form and at a high efficiency.

SUMMARY OF THE INVENTION

The present invention attempts to solve one more of the needs by providing a method of making an amino silicone nanoemulsion comprising the steps of:
a) mixing one or more liquid amino silicone compounds represented by formula (1) below with a solvent:

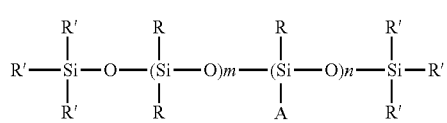

where each R is an alkyl group or a phenyl group with 1-10 carbon atoms, wherein each R' is an alkyl group having 1-10 carbon atoms, a phenyl group, a monovalent group represented by formula (2) below, or a monovalent group represented by the formula: —OR$^3$, where R$^3$ is a hydrogen atom or a monovalent hydrocarbon group with 1-10 carbon atoms; m is a whole number from 50-1000, n is a whole number from 1-100, A is a monovalent group represented by formula (2) below:

where R$^1$ and R$^2$ are divalent hydrocarbon groups with 1-10 carbon atoms; a is a whole number from 0-4;

b) mixing the mixture of amino silicone and solvent with surfactant, water, and, optionally, a protonating agent, to form a nanoemulsion;

c) dividing the nanoemulsion into a first nanoemulsion and a second nanoemulsion;

d) mixing the second nanoemulsion with a non-resin crosslinking agent
   i. at a temperature ranging from about 20° C. to about 100° C.;
   ii. wherein the non-resin crosslinking agent is represented by formula (3):

wherein n≥2, R is a polyvalent, saturated or unsaturated, substituted or unsubstituted, organic moiety comprising 2-30 carbon atoms, and the L groups, which may be identical or different, are functional groups capable of reacting with amino groups;
   iii. wherein the molar ratio of the non-resin crosslinking agent to the liquid amino silicone compound in the second nanoemulsion is from about 0.05:1 to about 10:1, preferably from about 0.1:1 to about 5:1, more preferably from about 0.5:1 to about 3:1;

e) mixing the first nanoemulsion with the second nanoemulsion to form a third nanoemulsion.

The invention also relates to methods of using the amino silicone nanoemulsions that are made by the described methods, as well as methods of making treatment compositions comprising the amino silicone nanoemulsions and methods of treating surfaces with treatment compositions comprising the amino silicone nanoemulsions.

DETAILED DESCRIPTION OF THE INVENTION

Features and benefits of the various embodiments of the present invention will become apparent from the following description, which includes examples of specific embodiments intended to give a broad representation of the invention. Various modifications will be apparent to those skilled in the art from this description and from practice of the invention. The scope is not intended to be limited to the particular forms disclosed and the invention covers all modifications, equivalents, and alternatives falling within the spirit and scope of the invention as defined by the claims.

As used herein, the articles including "the," "a" and "an" when used in a claim or in the specification, are understood to mean one or more of what is claimed or described.

As used herein, the terms "include," "includes" and "including" are meant to be non-limiting.

The term "substantially free of" or "substantially free from" as used herein refers to either the complete absence of an ingredient or a minimal amount thereof merely as impurity or unintended byproduct of another ingredient. A composition that is "substantially free" of/from a component means that the composition comprises less than about 0.5%, 0.25%, 0.1%, 0.05%, or 0.01%, or even 0%, by weight of the composition, of the component.

As used herein, the term nanoemulsion refers to thermal dynamically stable oil in water emulsions that have extremely small droplet sizes (below 350 nm, or typically below 250 nm). These materials have special properties, including optical translucency, very large dispersed phase surface-to-volume ratios and long term kinetic stability. Due to similarity in appearance, translucent nanoemulsions are sometimes confused with microemulsions, which belong to another class of stable (thermodynamically) and optically clear colloidal systems. Microemulsions are spontaneously formed by "solubilizing" oil molecules with a mixture of surfactants, co-surfactants and co-solvents. The required surfactant concentration in a microemulsion is several times higher than that in a nanoemulsion and significantly exceeds the concentration of the dispersed phase (generally, oil). Because of many undesirable side-effects caused by surfactants, this is disadvantageous or prohibitive for many applications. In addition, the stability of microemulsions is easily compromised by dilution, heating, or changing pH levels.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

All cited patents and other documents are, in relevant part, incorporated by reference as if fully restated herein. The citation of any patent or other document is not an admission that the cited patent or other document is prior art with respect to the present invention.

In this description, all concentrations and ratios are on a weight basis of the cleaning composition unless otherwise specified.

Method of Making an Amino Silicone Nanoemulsion

The present invention relates to a method of making an amino silicone nanoemulsion comprising the steps of:
a) mixing one or more liquid amino silicone compounds represented by formula (1) below with a solvent:

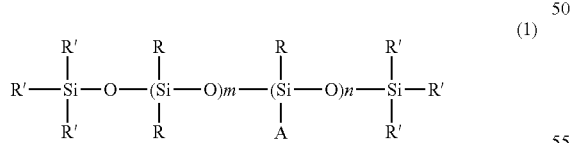

(1)

where each R is an alkyl group or a phenyl group with 1-10 carbon atoms,
wherein each R' is an alkyl group having 1-10 carbon atoms, a phenyl group, a monovalent group represented by formula (2) below, or a monovalent group represented by the formula: —OR$^3$, where R$^3$ is a hydrogen atom or a monovalent hydrocarbon group with 1-10 carbon atoms; m is a whole number from 50-1000, n is a whole number from 1-100,
A is a monovalent group represented by formula (2) below:

—R$^1$—(NH—R$^2$)$a$-NH$_2$ (2)

where R$^1$ and R$^2$ are divalent hydrocarbon groups with 1-10 carbon atoms;
a is a whole number from 0-4;
b) mixing the mixture of amino silicone and solvent with surfactant, water, and, optionally, a protonating agent, to form a nanoemulsion;
c) dividing the nanoemulsion into a first emulsion and a second emulsion;
d) mixing the second emulsion with a non-resin crosslinking agent
  i. at a temperature ranging from about 20° C. to about 100° C.;
  ii. wherein said non-resin crosslinking agent is represented by formula (3):

R-L$_n$ (3)

wherein n≥2, R is a polyvalent, saturated or unsaturated, substituted or unsubstituted, organic moiety comprising 2-30 carbon atoms, and the L groups, which may be identical or different, are functional groups capable of reacting with amino groups;
  iii. wherein the molar ratio of the non-resin crosslinking agent to the liquid amino silicone compound in the second emulsion is from about 0.05:1 to about 10:1, preferably from about 0.1:1 to about 5:1, more preferably from about 0.5:1 to about 3:1;
e) mixing the first nanoemulsion with the second nanoemulsion to form a third nanoemulsion.

The first nanoemulsion may be substantially free of a non-resin crosslinking agent.

In the methods described herein, the protonating agent may be mixed in before the step of mixing in the non-resin crosslinking agent. Or, the protonating agent may be mixed in after the step of mixing in the non-resin crosslinking agent. Example 1 (below) describes mixing protonating agent with a mixture of amino silicone and solvent, surfactant, and water, to form a nanoemulsion and then mixing the nanoemulsion with a crosslinker to produce a resulting nanoemulsion that has a reduced particle size. Example 2 (below) describes mixing a mixture of amino silicone and solvent with surfactant and water, to form an emulsion, then mixing this emulsion with a crosslinker, and finally mixing in a protonating agent to form the resulting nanoemulsion. The resulting nanoemulsions, in Example 2, have increased particle sizes, as compared to Example 1.

The method may further comprise the step of mixing the first nanoemulsion with a non-resin crosslinking agent:
  i. at a temperature ranging from about 20° C. to about 100° C.;
  ii. wherein the non-resin crosslinking agent is represented by formula (3):

R-L$_n$ (3)

wherein n≥2, R is a polyvalent, saturated or unsaturated, substituted or unsubstituted, organic moiety comprising 2-30 carbon atoms, and the L groups, which may be identical or different, are functional groups capable of reacting with amino groups;
  iii. wherein the molar ratio of the non-resin crosslinking agent to the liquid amino silicone compound in the first emulsion is from about 0.05:1 to about 10:1, preferably from about 0.1:1 to about 5:1, more preferably from about 0.5:1 to about 3:1.
When the method further comprises the step of mixing the first nanoemulsion with a non-resin crosslinking agent, the ratio of the non-resin crosslinking agent to the liquid amino silicone compound in the first emulsion may be different from the ratio of the non-resin crosslinking agent to the liquid amino silicone compound in the second emulsion.

The ratio of the first nanoemulsion to the second nanoemulsion in the third nanoemulsion may be from about 1:1 to about 12:1, preferably about 6:1.

Each of the first, second, and the third nanoemulsion may be substantially free of a silicone resin.

Amino Silicone Nanoemulsion

The amino silicone nanoemulsions made by the method disclosed herein provide a highly efficient deposition on a target surface. Benefits derived from this deposition may generally apply in the area of repellency of water and/or water-based compositions and/or oil and/or oil-based compositions, such as water-based stains and oily soils. Such benefits may be measured as an increased time to wick on fabrics, a reduced dry-time on hair and/or an increased contact angle on a hard surface. Without being bound by theory, it is believed that the amino silicone nanoemulsions disclosed herein comprise self-assembled, spherical, positively charged amino silicone nano-particles. These self-assembled, spherical, positively charged nano-particles exhibit efficient deposition and controlled spreading, forming a structured film on a surface that provides the repellency benefit. It is believed that crosslinking of the amino silicone nanoemulsion (e.g., at the ratio(s) of non-resin crosslinking agent to amino silicone compound described herein) further enhances the repellency benefits. And, mixing nanoemulsions having different degrees of crosslinking (in other words, different ratios of non-resin crosslinking agents to liquid amino silicone compounds) further enhances repellency.

The average particle sizes of the disclosed nanoemulsions range from about 20 nm to about 350 nm, or about 20 nm to about 250 nm, or about 20 nm to about 200 nm, or about 30 nm to about 140 nm, or about 50 nm to about 100 nm. (as measured by Malvern Zetasizer Nano Series instrument.).

Amino Silicone Compound

The amino silicone nanoemulsion of the present invention comprises from about 1% to about 45% of one or more liquid amino silicone compounds, by weight of the nanoemulsion. The amino silicone nanoemulsion may comprise from about 5% to about 30% of the amino silicone compounds, by weight of the nanoemulsion. The amino silicone nanoemulsion may comprise from about 10% to about 20% of the amino silicone compounds, by weight of the nanoemulsion.

The amino silicone compound may be represented by structural formula (1) below:

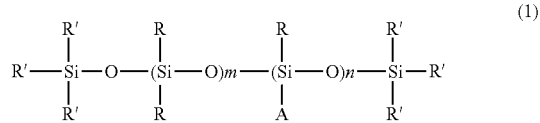

(1)

where each R group is independently selected from substituted or unsubstituted alkyl or aryl groups having 1-22 carbon atoms, each R' group is independently selected from substituted or unsubstituted alkyl or aryl groups having 1-22 carbon atoms, or monovalent groups represented by the formula: —$OR^3$, where $R^3$ is a hydrogen atom or a monovalent hydrocarbon group with 1-10 carbon atoms; m is a whole number from 20-1000, typically m is a whole number from 50-800; n is a whole number from 1-100, typically n is a whole number from 5-80.

A is a monovalent group represented by formula (2) below:

(2)

where each of $R^1$ and $R^2$ is independently selected from divalent hydrocarbon groups having 1-22 carbon atoms, more typically 1-8 carbon atoms, even more typically 1-4 carbon atoms. Suitable $R^1$ and $R^2$ groups include methylene groups, ethylene groups, trimethylene groups, tetramethylene groups, or other alkylene groups. Each of $R^1$ and $R^2$ may be a methylene group; a is a whole number from 0-4, typically a is a whole number from 0-2, more typically, a is 0 or 1.

One species of amino silicone compound may be used alone or two or more species may be used together.

Examples of suitable A groups include —$CH_2$—$NH_2$, —$(CH_2)_2$—$NH_2$, —$(CH_2)_3$—$NH_2$, —$(CH_2)_2$—NH—$(CH_2)_3NH_2$, —$(CH_2)_3$—NH—$(CH_2)_2NH_2$, —$(CH_2)_3$—HN—$(CH_2)_3NH_2$, and —$(CH_2)_3$—NH—$(CH_2)_3$—NH—$(CH_2)_3$—$NH_2$.

In the amino silicone compound of formula (1), the ratio of m/n may be less than about 100, or m/n is less than about 90, or m/n is less than about 80.

The amino silicone compound may be represented by general formula (1), where each R is a methyl group, each R' is a methyl group, A is a propyl amino, and m/n is about 70.

From about 1% to about 20% of the terminal R' groups in the amino silicone compound represented by general formula (1) may be monovalent groups represented by the formula: —$OR^3$, where $R^3$ is a hydrogen atom or a monovalent hydrocarbon group with 1-10 carbon atom.

The viscosity of the amino silicone compound may be from about 10 mPa·s, at 25° C., or from about 50 mPa·s, to about 100,000 mPa·s, or to about 10,000 mPa·s. The polyorgansiloxane compound may have a viscosity of from about 200 mPa·s to about 500 mPa·s, at 25° C.

Non-Resin Crosslinking Agent

Non-resin crosslinking agents (also referred to herein as non-resin crosslinkers) are molecules with two or more functional groups that join chains of amino silicones. Without being bound by theory, it is believed that the crosslinking agent covalently binds to the amino silicone via the amino group. Thus, the crosslinking agent may be difunctional, trifunctional, tetrafunctional, or otherwise polyfunctional. A variety of crosslinking agents may be used in the amino silicone nanoemulsion.

The non-resin crosslinking agent may be represented by formula (3):

(3)

wherein n≥2, R is a polyvalent, saturated or unsaturated, substituted or unsubstituted, organic moiety comprising 2-30 carbon atoms, and the L groups, which may be identical or different, are functional groups capable of reacting with amino groups;

Nonlimiting examples of L groups include saturated or unsaturated, substituted or unsubstituted alkyl, aryl, alkylaryl halides, substituted or unsubstituted, saturated or unsaturated $C_1$-$C_{30}$ esters, substituted or unsubstituted di(meth)acrylates or oligo(meth)acrylates, substituted or unsubstituted $C_1$-$C_{30}$ acrylates, and substituted or unsubstituted $C_1$-$C_{30}$ epoxides.

R may be a polyvalent, saturated or unsaturated, substituted or unsubstituted, organic moiety comprising 2-15 carbon atoms, preferably a polyvalent, saturated or unsaturated, substituted or unsubstituted, alkyl group comprising 2-15 carbon atoms, more preferably a polyvalent, saturated or unsaturated, substituted or unsubstituted, alkyl group comprising 2-10 carbon atoms. The non-resin crosslinking agent of formula (3) may comprise at least two identical L groups.

The non-resin crosslinking agent may be selected from the group consisting of alkyl poly-halides, preferably alkyl dihalides, more preferably $C_2$-$C_{30}$ alkyl dihalides, saturated or unsaturated esters, for example, saturated or unsaturated diesters, preferably saturated or unsaturated $C_2$-$C_{30}$ diesters, more preferably $C_2$-$C_{30}$ dimethylesters, $C_2$-$C_{30}$ diethylesters, and $C_2$-$C_{30}$ divinyl esters, saturated or unsaturated $C_2$-$C_{30}$ di-, tri-, and polycarboxylic acids, substituted or unsubstituted epoxides, preferably diepoxides, more preferably $C_2$-$C_{30}$ diepoxide, substituted or unsubstituted acrylates, preferably substituted or unsubstituted di(meth)acrylates or oligo(meth)acrylates, and mixtures thereof. The non-resin crosslinking agent may be selected from the group consisting of alkyl di-iodides, alkyl dichlorides, alkyl dibromides, and mixtures thereof. The non-resin crosslinking agent may be selected from the group consisting of dibromopropane, 1,4-dibromobutane, 1,6-dibromohexane, 1,12-dibromo-dodecane, 1,4-dichloro-2-butene, dichloro-o-xylene, dichloro-m-xylene, dichloro-p-xylene, and mixtures thereof. The non-resin crosslinking agent may be selected from the group consisting of activated esters, for example, vinyl esters of di-, tri-, or poly-acid compounds, such as divinyladipate. The non-resin crosslinking agent may be selected from the group consisting of dimethyl adipate (DMA), divinyl adipate (DVA), and mixtures thereof.

The non-resin crosslinking agent may be selected from the group consisting of etheylene glycol diepoxide, propylylene glycol diepoxide, hexanediol diepoxide, epichlorohydrin, and butanediol diepoxide.

The non-resin crosslinking agent may be selected from $C_1$-$C_{30}$ alcohol esters of carboxylic acids, such as citric acid or $C_2$-$C_{30}$ dicarboxylic acids, e.g., oxalic acid, malonic acid, succinic acid, glutaric acid, adipic acid, pimelic acid, suberic acid, azelaic acid, and sebacic acid.

Suitable examples of unsubstituted di(meth)acrylates are: hexanediol diacrylate, butanediol diacrylate, GX-8370 (Siber-Hegner), 1,3-butanedioldimethacrylate, and neopentyl glycol diacrylate.

Suitable examples of substituted di(meth)acrylates are: 1-acryloxy 2-hydroxy 3-methacryloxpropane, 2,2-dimethylpropyl 2,2-dimethylpropionate diacrylate, pentaerythritol diacrylate monostearate, polyethylene glycol-400 diacrylate, polyethylene glycol-300 diacrylate, polypropylene glycol-400 diacrylate, tetraethylene glycol diacrylate, polypropylene glycol-700 diacrylate, 2,2-bis[-4-(acryloxydiethoxy)phenyl]propane, triethylene glycol diacrylate, tripropylene glycol diacrylate, SR 349 (Sartomer), polyethylene glycol-600 diacrylate, and propoxylated neopentyl glycol diacrylate.

A suitable example of an unsubstituted oligo(meth)acrylate is trimethylolpropane triacrylate.

Suitable examples of substituted oligo(meth)acrylates are: M-325 (Siber-Hegner), dipentaerythritol pentaacrylate and hexaacrylate, A-TMMT (Siber-Hegner), tetramethylolmethane triacrylate, trimethylolmethanol triacrylate, trimethylolpropane ethoxylate triacrylate, tris(acryloyloxyethyl) phosphate, tris(2-hydroxyethyl)isocyanurate triacrylate, ethoxylated trimethylolpropane triacrylate, propoxylated trimethylolpropane triacrylate, propoxylated glyceryl triacrylate, di(trimethylolpropane) tetraacrylate, di(pentaerythritol) pentaacrylate, pentaerythritol triacrylate, and ethoxylated pentaerythritol tetraacrylate.

Suitable examples of unsubstituted mono(meth)acrylates are methyl acrylate, ethyl acrylate, butyl acrylate, methyl methacrylate, cyclohexyl acrylate, isobornyl acrylate, lauryl acrylate, stearyl acrylate, ethylhexyl acrylate, tridecyl acrylate, isooctyl acrylate.

Suitable examples of substituted mono(meth)acrylates or related compounds are: perfluoroalkylethyl acrylate (Fluowet AC 812, Hoechst AG), 2-acrylamido-2-methyl-1-propanesulfonic acid (Lubrizol), 2-acryloyloxyethyl hydrogen phthalate (Viscoat 2000, Siber-Hegner GmbH), beta-acryloyloxyethyl hydrogen succinate (ASA, Siber-hegner GmbH), acryloyloxyethylphosphoric acid (Lightester Pa., Toagosei), 2-acryloyloxypropyl hydrogen phthalate (Viscoat 2100, Siber-Hegner GmbH), the potassium salt of (3-sulfopropyl) acrylate, the dipotassium salt of bis(3-sulfopropyl) itaconate, N,N-dimethyl-N-methacryloxaethyl-N-(3-sulfopropyl)ammonium betaine, 2-carboxyethyl acrylate, 2-hydroxyethyl acrylate, 2-ethylthioethyl methacrylate, acrylamide, methyl 2-acrylamido-2-methoxyacetate, acrylonitrile, (2-(acryl-oxy)ethyl)(4-benzenebenzyl)dimethylammonium bromide, (2-hydroxyethyl) acrylate, acryloxydimethylbutyrolactone, acrylic acid, methoxypolyethylene glycol-400 acrylate, nonylphenol ethoxylate acrylate (N-117E, Siber-Hegner), nonylphenol diethoxylate acrylate, phenoxydiethylene glycol acrylate, phenoxyethyl acrylate, dimethylaminoethyl acrylate, methyl chloride salt of dimethylaminoethyl acrylate, glycidyl acrylate, phenoxypolyethylene glycol acrylate, 2,2,3,3-tetrafluoropropyl acrylate, methoxypolyethylene glycol-1000 methacrylate, tetrahydrofurfuryl acrylate, caprolactone acrylate, 2(2-ethoxyethoxy)ethyl acrylate, 2-acrylamidoglycolic acid.

The molar ratio of the non-resin crosslinking agent to the liquid amino silicone compound is from about 0.05:1 to about 10:1, preferably from about 0.1:1 to about 5:1, more preferably from about 0.5:1 to about 3:1.

Silicone Resin

Typically, the amino silicone nanoemulsion of the present disclosure is substantially free of a silicone resin.

An example of a silicone resin is a mixture of polyorganosiloxane-silicone resins, where each of the one or more silicone resins of the polyorganosiloxane-silicone resin mixture contains at least about 80 mol % of units selected from the group consisting of units of the general formulas 3, 4, 5, 6:

$$R^4{}_3SiO_{1/2} \quad (3),$$

$$R^4{}_2SiO_{2/2} \quad (4),$$

$$R^4SiO_{3/2} \quad (5),$$

$$SiO_{4/2} \quad (6),$$

in which $R^4$ is selected from H, —OR, or —OH residues or monovalent hydrocarbon residues with 1 to 40 carbon atoms, optionally substituted with halogens, where at least 20 mol % of the units are selected from the group consisting of units of the general formulas 5 and 6, and a maximum of 10 wt % of the $R^4$ residues are —OR and —OH residues.

Solvent

The amino silicone nanoemulsion of the present invention comprises from about 0.1% to about 50% of one or more solvents, by weight of the amino silicone. The amino silicone nanoemulsion may comprise from about 0.1% to about 40% of one or more solvents, by weight of the amino silicone. The amino silicone nanoemulsion may comprise from about 1% to about 30%, or about 1% to about 25%, or about 1% to about 20% of one or more solvents, by weight of the amino silicone. The amino silicone nanoemulsion may comprise from about 1% to about 15% or from about 2% to about 10% of one or more solvents, by weight of the amino silicone. The amino silicone nanoemulsion may comprise from about 0.1% to about 5% of one or more solvents, by weight of the amino silicone. The amino silicone nanoemulsion may comprise from about 1% to about 5% or from about 2% to about 5% of one or more solvents, by weight of the amino silicone.

The solvent is selected from monoalcohols, polyalcohols, ethers of monoalcohols, ethers of polyalcohols, or mixtures thereof. Typically, the solvent has a hydrophilic-lipophilic balance (HLB) ranging from about 6 to about 14. More typically, the HLB of the solvent will range from about 8 to about 12, most typically about 11. One type of solvent may be used alone or two or more types of solvents may be used together.

The solvent may comprise a glycol ether, an alkyl ether, an alcohol, an aldehyde, a ketone, an ester, or a mixture thereof.

The solvent may be selected from a monoethylene glycol monoalkyl ether that comprises an alkyl group having 4-12 carbon atoms, a diethylene glycol monoalkyl ether that comprises an alkyl group having 4-12 carbon atoms, or a mixture thereof. Suitable alkyl groups include butyl groups, hexyl groups, heptyl groups, octyl groups, 2-ethylhexyl groups, nonyl groups, decyl groups, undecyl groups, and dodecyl groups. The alkyl group may be a hexyl group, e.g., diethylene glycol monohexyl ether or ethylene glycol monohexyl ether.

Suitable examples of monoethylene glycol monoalkyl ethers and diethylene glycol monoalkyl ethers include ethylene glycol monobutyl ether, ethylene glycol monohexyl ether, ethylene glycol monooctyl ether, ethylene glycol monodecyl ether, and ethylene glycol monododecyl etherdiethylene glycol monobutyl ether, diethylene glycol monohexyl ether, diethylene glycol monooctyl ether, diethylene glycol monodecyl ether, and diethylene glycol monododecyl ether. The solvent may be ethylene glycol monohexyl ether, diethylene glycol monohexyl ether, or a mixture thereof.

The solvent may comprise an ethylene glycol monoalkyl ether that comprises an alkyl group having 4-12 carbon atoms, a diethylene glycol monoalkyl ether that comprises an alkyl group having 4-12 carbon atoms, an ethylene glycol monohexyl ether, an ethylene glycol monobutyl ether, a diethylene glycol monohexyl ether, a diethylene glycol monobutyl ether, or combinations thereof.

Surfactant

The amino silicone nanoemulsion of the present invention comprises from about 1% to about 50% of one or more surfactants, by weight of the amino silicone. The amino silicone nanoemulsion may comprise from about 1% to about 40%, or from about 1% to about 30%, or from about 1% to about 25%, or from about 1% to about 20% of one or more surfactants, by weight of the amino silicone. The amino silicone nanoemulsion may comprise from about 5% to about 20% or from about 10% to about 20% of one or more surfactants, by weight of the amino silicone. The surfactant is selected from anionic surfactants, nonionic surfactants, cationic surfactants, zwitterionic surfactants, amphoteric surfactants, ampholytic surfactants, or mixtures thereof. The amino silicone nanoemulsion of the present disclosure may comprise a nonionic surfactant, a cationic surfactant, or a mixture thereof. The amino silicone nanoemulsion of the present disclosure may comprise a nonionic surfactant. It is believed that surfactant facilitates uniform dispersing of the amino silicone fluid compound and the solvent in water.

Nonionic Surfactants

Suitable nonionic surfactants useful herein may comprise any conventional nonionic surfactant. More specific examples of suitable nonionic surfactants include, for example, polyoxyethylene alkyl ethers, polyoxyethylene polyoxypropylene alkyl ethers or other polyoxyalkylene alkyl ethers; polyoxyethylene alkylphenyl ethers; polyoxyethylene alkyl esters; polyoxyethylene alkyl phenyl ether sorbitan esters; glycerin esters; sorbitan fatty acid esters; sucrose fatty acid esters or other polyhydric alcohol fatty acid esters; ethoxylated fatty acids; and ethoxylated fatty acid amides. The nonionic surfactant may be selected from polyoxyethylene alkyl ethers, polyoxyethylene polyoxypropylene alkyl ethers, or a mixture thereof. Typically, total HLB (hydrophilic-lipophilic balance) of the nonionic surfactant that is used is in the range of about 8-16, more typically in the range of 10-15.

Other non-limiting examples of nonionic surfactants useful herein include alkoxylated fatty alcohols, e.g., ethoxylated nonionic surfactant, and amine oxide surfactants. These materials are described in U.S. Pat. No. 4,285,841, Barrat et al, issued Aug. 25, 1981. The nonionic surfactant may be selected from the ethoxylated alcohols and ethoxylated alkyl phenols of the formula $R(OC_2H_4)_nOH$, wherein R is selected from the group consisting of aliphatic hydrocarbon radicals containing from about 8 to about 15 carbon atoms and alkyl phenyl radicals in which the alkyl groups contain from about 8 to about 12 carbon atoms, and the average value of n is from about 5 to about 15. These surfactants are more fully described in U.S. Pat. No. 4,284,532, Leikhim et al, issued Aug. 18, 1981. Further non-limiting examples of nonionic surfactants useful herein include: $C_{12}$-$C_{18}$ alkyl ethoxylates, such as, NEODOL® nonionic surfactants from Shell; $C_6$-$C_{12}$ alkyl phenol alkoxylates wherein the alkoxylate units are a mixture of ethyleneoxy and propyleneoxy units; $C_{12}$-$C_{18}$ alcohol and $C_6$-$C_{12}$ alkyl phenol condensates with ethylene oxide/propylene oxide block polymers such as Pluronic® from BASF; $C_{14}$-$C_{22}$ mid-chain branched alcohols, BA, as discussed in U.S. Pat. No. 6,150,322; $C_{14}$-$C_{22}$ mid-chain branched alkyl alkoxylates, $BAE_x$, wherein x is from 1 to 30, as discussed in U.S. Pat. No. 6,153,577, U.S. Pat. No. 6,020,303 and U.S. Pat. No. 6,093,856; Alkylpolysaccharides as discussed in U.S. Pat. No. 4,565,647 to Llenado, issued Jan. 26, 1986; specifically alkylpolyglycosides as discussed in U.S. Pat. No. 4,483,780 and U.S. Pat. No. 4,483,779; Polyhydroxy fatty acid amides as discussed in U.S. Pat. No. 5,332,528, WO 92/06162, WO 93/19146, WO 93/19038, and WO 94/09099; and ether capped poly(oxyalkylated) alcohol surfactants as discussed in U.S. Pat. No. 6,482,994 and WO 01/42408.

Cationic Surfactants

The amino silicone nanoemulsion of the present invention may comprise a cationic surfactant. The amino silicone nanoemulsion may comprise from about 1% to about 50% of a cationic surfactant, by weight of the amino silicone. The amino silicone nanoemulsion may comprise from about 1% to about 40% or from about 1% to about 30% of a cationic surfactant, by weight of the amino silicone. The amino silicone nanoemulsion may comprise from about 2% to about 20% or from about 2% to about 15% of a cationic surfactant, by weight of the amino silicone. The cationic surfactant may have an HLB of from about 18 to about 25.

Cationic surfactants include, for example, alkyl trimethylammonium chloride, alkylamine hydrochloric acid salts, alkylamine acetate, alkylbenzene dimethyl ammonium chloride and the like.

Non-limiting examples of cationic surfactants include: the quaternary ammonium surfactants, which can have up to 26 carbon atoms include: alkoxylate quaternary ammonium (AQA) surfactants as discussed in U.S. Pat. No. 6,136,769; dimethyl hydroxyethyl quaternary ammonium as discussed in U.S. Pat. No. 6,004,922; dimethyl hydroxyethyl lauryl ammonium chloride; polyamine cationic surfactants as discussed in WO 98/35002, WO 98/35003, WO 98/35004, WO 98/35005, and WO 98/35006; cationic ester surfactants as discussed in U.S. Pat. Nos. 4,228,042, 4,239,660 4,260,529 and U.S. Pat. No. 6,022,844; and amino surfactants as discussed in U.S. Pat. No. 6,221,825 and WO 00/47708, specifically amido propyldimethyl amine (APA).

Anionic Surfactants

Suitable anionic surfactants include sulphate and sulphonate surfactants. Suitable sulphonate surfactants include alkyl benzene sulphonate, e.g., $C_{10-13}$ alkyl benzene sulphonate. Suitable alkyl benzene sulphonate (LAS) may be obtained, by sulphonating commercially available linear alkyl benzene (LAB); suitable LAB includes low 2-phenyl LAB, such as those supplied by Sasol under the tradename Isochem® or those supplied by Petresa under the tradename Petrelab®, other suitable LAB include high 2-phenyl LAB, such as those supplied by Sasol under the tradename Hyblene®. A suitable anionic surfactant is alkyl benzene sulphonate that is obtained by DETAL catalyzed process, although other synthesis routes, such as HF, may also be suitable. A magnesium salt of LAS may be used.

Suitable sulphate surfactants include alkyl sulphate, e.g., $C_{8-18}$ alkyl sulphate, or predominantly $C_{12}$ alkyl sulphate.

Another suitable sulphate surfactant may be alkyl alkoxylated sulphate, for example, alkyl ethoxylated sulphate, such as a $C_{8-18}$ alkyl alkoxylated sulphate. Another suitable sulphate surfactant may be a $C_{8-18}$ alkyl ethoxylated sulphate. The alkyl alkoxylated sulphate may have an average degree of alkoxylation of from 0.5 to 20, or from 0.5 to 10. The alkyl alkoxylated sulphate may be a $C_{8-18}$ alkyl ethoxylated sulphate having an average degree of ethoxylation of from 0.5 to 10, from 0.5 to 7, from 0.5 to 5 or even from 0.5 to 3.

The alkyl sulphate, alkyl alkoxylated sulphate, and alkyl benzene sulphonates may be linear or branched, substituted or un-substituted.

The surfactant may be a mid-chain branched surfactant, e.g., a mid-chain branched anionic detersive surfactant, such as a mid-chain branched alkyl sulphate and/or a mid-chain branched alkyl benzene sulphonate. The mid-chain branches may be $C_{1-4}$ alkyl groups, typically methyl and/or ethyl groups.

Zwitterionic Surfactants

Examples of zwitterionic surfactants include: derivatives of secondary and tertiary amines, derivatives of heterocyclic secondary and tertiary amines, or derivatives of quaternary ammonium, quaternary phosphonium or tertiary sulfonium compounds. See U.S. Pat. No. 3,929,678 at column 19, line 38 through column 22, line 48, for examples of zwitterionic surfactants; betaines, including alkyl dimethyl betaine and cocodimethyl amidopropyl betaine, $C_8$ to $C_{18}$ (for example from $C_{12}$ to $C_{18}$) amine oxides. and sulfo and hydroxy betaines, such as N-alkyl-N,N-dimethylammino-1-propane sulfonate where the alkyl group can be $C_8$ to $C_{18}$ and in certain embodiments from $C_{10}$ to $C_{14}$.

Ampholytic Surfactants

Specific, non-limiting examples of ampholytic surfactants include: aliphatic derivatives of secondary or tertiary amines, or aliphatic derivatives of heterocyclic secondary and tertiary amines in which the aliphatic radical can be straight- or branched-chain. One of the aliphatic substituents may contain at least about 8 carbon atoms, for example from about 8 to about 18 carbon atoms, and at least one contains an anionic water-solubilizing group, e.g. carboxy, sulfonate, sulfate. See U.S. Pat. No. 3,929,678 at column 19, lines 18-35, for suitable examples of ampholytic surfactants.

Amphoteric Surfactants

Amphoteric surfactants include, for example, N-acylamidopropyl-N,N-dimethyl ammonia betaines, N-acylamidopropyl-N,N'-dimethyl-N'-β-hydroxypropyl ammonia betaines, and the like.

Examples of amphoteric surfactants include: aliphatic derivatives of secondary or tertiary amines, or aliphatic derivatives of heterocyclic secondary and tertiary amines in which the aliphatic radical can be straight- or branched-chain. One of the aliphatic substituents contains at least about 8 carbon atoms, typically from about 8 to about 18 carbon atoms, and at least one contains an anionic water-solubilizing group, e.g. carboxy, sulfonate, sulfate. Examples of compounds falling within this definition are sodium 3-(dodecylamino)propionate, sodium 3-(dodecylamino) propane-1-sulfonate, sodium 2-(dodecylamino) ethyl sulfate, sodium 2-(dimethylamino) octadecanoate, disodium 3-(N-carboxymethyldodecylamino)propane 1-sulfonate, disodium octadecyl-imminodiacetate, sodium 1-carboxymethyl-2-undecylimidazole, and sodium N,N-bis (2-hydroxyethyl)-2-sulfato-3-dodecoxypropylamine. See U.S. Pat. No. 3,929,678 to Laughlin et al., issued Dec. 30, 1975 at column 19, lines 18-35, for examples of amphoteric surfactants.

Other Surfactants

Polyester modified silicone or other silicone surfactants may also be optionally used in small amounts, e.g., less than 5%.

Water

The amino silicone nanoemulsion comprises from about 10% to about 99.99%, of water, by weight. The amino silicone nanoemulsion may include water in amounts of from about 10% to about 50%, by weight. In a concentrated consumer product, such as a laundry detergent or a shampoo, the amino silicone nanoemulsion may include water in amounts of from about 20% to about 90%, by weight. In a diluted consumer product being used as a treatment composition, the amino silicone nanoemulsion may include water in amounts of from about 20% to about 99.99%, by weight.

Protonating Agent

The protonating agent is generally a monoprotic or multiprotic, water-soluble or water-insoluble, organic or inorganic acid. Suitable protonating agents include, for example, formic acid, acetic acid, propionic acid, malonic acid, citric acid, hydrochloric acid, sulfuric acid, phosphoric acid, nitric acid, or a mixture thereof. The protonating agent may be selected from formic acid, acetic acid, or a mixture thereof. The protonating agent may be acetic acid. Generally, the acid is added in the form of an acidic aqueous solution.

The protonating agent is added in an amount necessary to achieve a nanoemulsion pH of from about 3.5 to about 11.0. The amino silicone nanoemulsions may comprise the protonating agent in an amount necessary to achieve a pH of from about 3.5 to about 6.5 or about 4.0 to about 6.0. The amino silicone nanoemulsinos may comprise the protonating agent in an amount necessary to achieve a pH of from about 5.0 to about 6.0 or about 5.5. The pH of the amino silicone nanoemulsion may be from about 3.5 to about 10.5 or about 4.0 to about 10.0. The pH of the amino silicone nanoemulsion may be from about 5.0 to about 9.0 or about 6.0 to about 8.0. The pH of the amino silicone nanoemulsion may be less than about 10.5.

Stabilizer

The amino silicone nanoemulsions may also comprise auxiliary stabilizers selected from mono- or polyalcohols and ethers thereof, which have a boiling point or boiling range of at most 260° C. at 0.10 MPa. Examples of monoalcohols are ethanol, n-propanol, isopropanol and butanol. Examples of polyalcohols are ethylene glycol and propylene glycol. Examples of polyalcohol ethers are ethylene glycol monobutyl ether, ethylene glycol monoethyl ether and diethylene glycol monoethyl ether. If used, the nanoemulsions may include auxiliary stabilizers at levels up to about 10%. Certain embodiments of the nanoemulsions optionally comprise from about 1% to about 7%, while others optionally comprise from about 2% to about 5% of the auxiliary stabilizer.

Optional Nanoemulsion Adjunct Ingredients

The amino silicone nanoemulsions may additionally include further substances, such as preservatives, scents, corrosion inhibitors and dyes. Examples of preservatives are alcohols, formaldehyde, parabens, benzyl alcohol, propionic acid and salts thereof and also isothiazolinones. The nanoemulsions may further include yet other additives, such as non-silicon-containing oils and waxes. Examples thereof are rapeseed oil, olive oil, mineral oil, paraffin oil or non-silicon-containing waxes, for example carnauba wax and candelilla wax or montan acid and montan ester waxes, incipiently oxidized synthetic paraffins, polyethylene waxes, polyvinyl ether waxes and metal-soap-containing waxes. The amino silicone nanoemulsions may further comprise carnauba wax, paraffin wax, polyethylene wax, or a mixture thereof. The nanoemulsions may comprise up to about 5% by weight of the nanoemulsion or from about 0.05% to about 2.5% by weight of the nanoemulsion of such further substances.

Treatment Composition

The amino silicone nanoemulsions of the present invention may be incorporated into treatment compositions or cleaning compositions, such as, but not limited to, a fabric care composition, a dish cleaning composition, a home care composition, a beauty care composition, or a personal care composition. The treatment composition may comprise from about 0.001% to about 99% by weight of the composition, of the amino silicone nanoemulsion. The treatment composition may comprise from about 0.001% to about 15% of the amino silicone nanoemulsion, by weight of the composition.

Examples of treatment and cleaning compositions include, but are not limited to, liquid laundry detergents, solid laundry detergents, laundry soap products, laundry spray treatment products, laundry pre-treatment products, fabric enhancer products, hand dish washing detergents, automatic dishwashing detergents, a beauty care detergent, hard surface cleaning detergents (hard surfaces include exterior surfaces, such as vinyl siding, windows, and decks), carpet cleaning detergents, conditioners, a shampoo, shave preparation products, and a household cleaning detergent. Examples of fabric care compositions suitable for the present disclosure include, but are not limited to, liquid laundry detergents, heavy duty liquid laundry detergents, solid laundry detergents, laundry soap products, laundry spray treatment products, laundry pre-treatment products, laundry soak products, heavy duty liquid detergents, and rinse additives. Examples of suitable dish cleaning compositions include, but are not limited to, automatic dishwasher detergents, detergents for hand washing of dishes, liquid dish soap, and solid granular dish soap. Examples of suitable home care compositions include, but are not limited to, rug or carpet cleaning compositions, hard surface cleaning detergents, floor cleaning compositions, window cleaning compositions, household cleaning detergents, and car washing detergents. Examples of suitable personal care compositions include, but are not limited to, beauty care cleansers, such as hair and skin cleansers, beauty bars, bar soap, bath beads, bath soaps, hand washing compositions, body washes and soaps, shampoo, conditioners, cosmetics, hair removal compositions, and oral care compositions.

The treatment composition may be provided in combination with a nonwoven substrate, as a treatment implement.

The compositions may provide water and/or oil repellency to the treated surface, thereby reducing the propensity of the treated surface to become stained by deposited water- or oil-based soils.

By "surfaces" it is meant any surface. These surfaces may include porous or non-porous, absorptive or non-absorptive substrates. Surfaces may include, but are not limited to, celluloses, paper, natural and/or synthetic textiles fibers and fabrics, imitation leather and leather, hair and skin. The present invention may be applied to natural and/or synthetic textile fibers and fabrics.

By "treating a surface" it is meant the application of the composition onto the surface. The application may be performed directly, such as spraying or wiping the composition onto a hard surface. The composition may or may not be rinsed off, depending on the desired benefit.

The present invention also encompasses the treatment of a fabric as the surface. This can be done either in a "pretreatment mode", where the composition is applied neat onto the fabric before the fabrics are washed or rinsed, or a "post-treatment mode", where the composition is applied neat onto the fabric after the fabric is washed or rinsed. The treatment may be performed in a "soaking mode", where the fabric is immersed and soaked in a bath of neat or diluted composition. The treatment may also be performed in a "through the wash" or "through the rinse" mode where the treatment composition, as defined herein, is added to the wash cycle or the rinse cycle of a typical laundry wash machine cycle. When used in the wash or rinse cycle, the compositions are typically used in a diluted form. By "diluted form" it is meant that the compositions may be diluted in the use, preferably with water at a ratio of water to composition up to 500:1, or from 5:1 to 200:1, or from 10:1 to 80:1.

Such treatment compositions may comprise carriers, which may be any known material that is useful in delivering the treatment compositions to the surface to be treated. The carrier may be as simple as a single component delivery vehicle, such as water or alcohol, which would allow the nanoemulsion to be sprayed onto a surface. Alternatively, the carrier may be complex, such as a cleaning composition, e.g., a laundry detergent where the nanoemulsion would be applied in conjunction with the other beneficial uses of the complex carrier.

Such treatment compositions may comprise various other materials, including bleaching agents, bleach activators, detersive surfactants, builders, chelating agents, smectite clays, dye transfer inhibiting agents, dispersants, enzymes, and enzyme stabilizers, catalytic metal complexes, polymeric dispersing agents, clay and soil removal/anti-redeposition agents, brighteners, suds suppressors, suds boosters, dyes, additional perfumes and perfume delivery systems, structure elasticizing agents, fabric softeners, carriers, hydrotropes, processing aids and/or pigments.

Detersive Surfactants—The treatment compositions according to the present disclosure may comprise a detersive surfactant or detersive surfactant system. Suitable detersive surfactants include nonionic surfactant, anionic surfactant, cationic surfactant, ampholytic surfactant, zwitterionic surfactant, semi-polar nonionic surfactant, or a mixture thereof. The detersive surfactant is typically present at a level of from about 0.1%, from about 1%, or even from about 5%, by weight of the treatment composition, to about 99.9%, to about 80%, to about 35%, or even to about 30%, by weight of the treatment composition. The specific surfactants described above, in the context of the nanoemulsion itself, may be included in the treatment compositions as detersive surfactants. When included in the treatment compositions (as opposed to the nanoemulsion itself), these surfactants are generally included at appropriate concentrations such that the surfactants provide a detersive or cleaning benefit.

Builders—The treatment compositions of the present disclosure may comprise one or more detergent builders or builder systems. When present, the compositions will typically comprise at least about 1% builder, or from about 5% or 10% to about 80%, 50%, or even 30% by weight, of said builder. Builders include, but are not limited to, the alkali metal, ammonium and alkanolammonium salts of polyphosphates, alkali metal silicates, alkaline earth and alkali metal carbonates, aluminosilicate builders polycarboxylate compounds, ether hydroxypolycarboxylates, copolymers of maleic anhydride with ethylene or vinyl methyl ether, 1,3, 5-trihydroxybenzene-2,4,6-trisulphonic acid, and carboxymethyl-oxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof.

Chelating Agents—The treatment compositions may also optionally contain one or more copper, iron and/or manganese chelating agents. If utilized, chelating agents will generally comprise from about 0.1% by weight of the compositions herein to about 15%, or even from about 3.0% to about 15% by weight of the compositions herein.

Dye Transfer Inhibiting Agents—The treatment compositions of the present disclosure may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole (PVPVI), polyvinyloxazolidones and polyvinylimidazoles or mixtures thereof. When present in the compositions herein, the dye transfer inhibiting agents are present at levels from about 0.0001%, from about 0.01%, from about 0.05% by weight of the cleaning compositions to about 10%, about 2%, or even about 1% by weight of the cleaning compositions.

Dispersants—The treatment compositions of the present disclosure may also contain dispersants. Suitable water-soluble organic materials are the homo- or co-polymeric acids or their salts, in which the polycarboxylic acid may comprise at least two carboxyl radicals separated from each other by not more than two carbon atoms.

Enzymes—The treatment compositions may comprise one or more detergent enzymes, which provide cleaning performance and/or fabric care benefits. Examples of suitable enzymes include, but are not limited to, hemicellulases, peroxidases, proteases, cellulases, xylanases, lipases, phospholipases, esterases, cutinases, pectinases, keratanases, reductases, oxidases, phenoloxidases, lipoxygenases, ligninases, pullulanases, tannases, pentosanases, malanases, ß-glucanases, arabinosidases, hyaluronidase, chondroitinase, laccase, and amylases, or mixtures thereof. A typical combination is a cocktail of conventional applicable enzymes like protease, lipase, cutinase and/or cellulase in conjunction with amylase.

Enzyme Stabilizers—Enzymes for use in the treatment compositions, e.g., detergents, may be stabilized by various techniques. The enzymes employed herein can be stabilized by the presence of water-soluble sources of calcium and/or magnesium ions in the finished compositions that provide such ions to the enzymes.

The treatment composition may comprise an amino silicone nanoemulsion and a carrier. Typically, the amino silicone nanoemulsion is substantially free of a silicone resin. The treatment composition may comprise an amino silicone nanoemulsion, a carrier, and a perfume, a detersive surfactant system, or a cleaning adjunct additive. The detersive surfactant system may comprise one or more surfactants selected from nonionic surfactants, cationic surfactants, anionic surfactants, zwitterionic surfactants, ampholytic surfactants, or amphoteric surfactants. The detersive surfactant system may comprise a surfactant selected from $C_{10}$-$C_{16}$ alkyl benzene sulfonates, $C_8$-$C_{18}$ alkyl sulfate, $C_8$-$C_{18}$ alkyl ethoxylated sulfate, or a mixture thereof.

The treatment composition may be a fabric care composition. Such a fabric care composition may take the form of detergent composition or a rinse added fabric conditioning compositions. Such compositions may comprise a fabric softening active and a dispersant polymer, to provide a stain repellency benefit to fabrics treated by the composition, typically from about 0.00001 wt. % (0.1 ppm) to about 1 wt. % (10,000 ppm), or even from about 0.0003 wt. % (3 ppm) to about 0.03 wt. % (300 ppm) based on total rinse added fabric conditioning composition weight. The compositions may be rinse added fabric conditioning compositions. Examples of typical rinse added conditioning composition can be found in U.S. Provisional Patent Application Ser. No. 60/687,582 filed on Oct. 8, 2004.

The treatment composition may be encapsulated in a water-soluble or water-dispersible pouch. The water-soluble film or pouch may comprise polyvinyl alcohol, polyvinyl acetate, or mixtures thereof. The unit dose form may comprise at least two compartments, or at least three compartments. At least one compartment may be superimposed on another compartment.

The treatment composition may be in the form of a granule. Granular treatment compositions may include any number of conventional detergent ingredients, such as the components described above, e.g., surfactants, chelants, enzymes. Granular detergent compositions typically comprise from about 1% to 95% by weight of a surfactant. Granular detergents can be made by a wide variety of processes, non-limiting examples of which include spray drying, agglomeration, fluid bed granulation, marumarisation, extrusion, or a combination thereof. Bulk densities of granular detergents generally range from about 300 g/l-1000 g/l. The average particle size distribution of granular detergents generally ranges from about 250 microns-1400 microns.

The treatment composition disclosed herein may be selected from a beauty care composition, a hand washing composition, a body wash composition, a shampoo composition, a conditioner composition, a cosmetic composition, a hair removal composition, a oral care composition, a laundry spray composition, a laundry rinse additive composition, a liquid laundry detergent compositions, a solid laundry detergent compositions, a hard surface cleaning compositions, a liquid hand dishwashing compositions, a solid automatic dishwashing compositions, a liquid automatic dishwashing, and a tab/unit dose form automatic dishwashing compositions, and a laundry detergent compositions contained in a water-soluble pouch.

Method of Making Treatment Composition Comprising Amino Silicone Nanoemulsion

The treatment compositions disclosed herein may be prepared by combining the components thereof in any convenient order and by mixing, e.g., agitating, the resulting component combination to form a phase stable cleaning composition. A liquid matrix may be formed containing at least a major proportion, or even substantially all, of the liquid components, e.g., nonionic surfactant, the non-surface active liquid carriers and other optional liquid components, with the liquid components being thoroughly admixed by imparting shear agitation to this liquid combination. For example, rapid stirring with a mechanical stirrer may usefully be employed. While shear agitation is maintained, substantially all of any anionic surfactant and the solid ingredients can be added. Agitation of the mixture is continued, and if necessary, can be increased at this point to form a solution or a uniform dispersion of insoluble solid phase particulates within the liquid phase. After some or all of the solid-form materials have been added to this agitated mixture, particles of any enzyme material to be included, e.g., enzyme prills are incorporated. As a variation of the composition preparation procedure described above, one or more of the solid components may be added to the agitated mixture as a solution or slurry of particles premixed with a minor portion of one or more of the liquid components. After addition of all of the composition components, agitation of the mixture is continued for a period of time sufficient to form compositions having the requisite viscosity and phase stability characteristics. Frequently this will involve agitation for a period of from about 30 to 60 minutes.

The amino silicone nanoemulsion may first be combined with one or more liquid components to form an aqueous amino silicone nanoemulsion premix, and this aqueous amino silicone nanoemulsion premix is added to a composition formulation containing a substantial portion, for example more than 50% by weight, more than 70% by weight, or even more than 90% by weight, of the balance of components of the cleaning composition. For example, in the methodology described above, both the aqueous amino silicone nanoemulsion premix and the enzyme component are added at a final stage of component additions. The aqueous amino silicone nanoemulsion may be encapsulated prior to addition to the detergent composition, the encapsulated aqueous amino silicone nanoemulsion is suspended in a structured liquid, and the suspension is added to a composition formulation containing a substantial portion of the balance of components of the cleaning composition.

Methods of Using Treatment Compositions

The treatment compositions of the present disclosure may be used in a method of treating a surface. The method of treating a surface comprises the step of applying the amino silicone nanoemulsion treatment composition of the present disclosure to a surface, where the surface is selected from fabric, skin, hair, or a hard surface.

Fabric Treatment

The treatment compositions disclosed in the present specification may be used to clean or treat a fabric, such as those described herein. Typically at least a portion of the fabric is contacted with an embodiment of the aforementioned fabric care compositions, in neat form or diluted in a liquor, for example, a wash liquor and then the fabric may be optionally washed and/or rinsed and/or dried without further treatment. A fabric may be optionally washed and/or rinsed, contacted with an embodiment of the aforementioned fabric care compositions and then optionally washed and/or rinsed. For purposes of the present disclosure, washing includes but is not limited to, scrubbing, and mechanical agitation. The fabric may comprise most any fabric capable of being laundered or treated.

The fabric care compositions disclosed in the present specification can be used to form aqueous washing or treatment solutions for use in the laundering and/or treatment of fabrics. Generally, an effective amount of such compositions is added to water, preferably in a conventional fabric laundering automatic washing machine, to form such aqueous laundering solutions. The aqueous washing solution so formed is then contacted, preferably under agitation, with the fabrics to be laundered therewith. An effective amount of the fabric care composition, such as the liquid detergent compositions disclosed in the present specification, may be added to water to form aqueous laundering solutions that may comprise from about 500 to about 7,000 ppm or even from about 1,000 to about 3,000 ppm of fabric care composition.

The fabric care compositions may be employed as a laundry additive, a pre-treatment composition and/or a post-treatment composition.

Without being bound by theory it is believed the treatment of a fabric with compositions disclosed in the present specification may increase the time-to-wick of the fabric. Table 1 shows an increase in the time-to-wick of cotton fabric as a result of treatment with examples of compositions disclosed in the present specification.

There is provided a method of treating a surface comprising the step of applying the amino silicone nanoemulsion treatment composition of the present disclosure to a surface, where the surface is a fabric and where the water repellency relative to the untreated fabric is increased, as measured by an increase in Time to Wick. The increase in Time to Wick may be greater than about 100 seconds, or greater than about 500 seconds, or greater than about 1200 seconds. The oil repellency relative to the untreated fabric may be increased, as measured by an increase in Time to Wick. The oil repellency relative to the untreated fabric may be increased, as measured by an increase in Time to Wick greater than about 10 seconds.

Hair Treatment

The treatment compositions disclosed in the present specification may be used to clean or treat hair. Typically at least a portion of the hair is contacted with an embodiment of the aforementioned hair care compositions, in neat form or diluted in a liquor, for example, a wash liquor, and then the hair may be optionally washed and/or rinsed and/or dried without further treatment. Hair may be optionally washed and/or rinsed, contacted with an embodiment of the aforementioned hair care compositions and then optionally washed and/or rinsed and/or dried without further treatment. For purposes of the present disclosure, washing includes but is not limited to, scrubbing, and mechanical agitation.

The hair care compositions disclosed in the present specification can be used to form aqueous washing or treatment solutions for use in the washing and/or treatment of hair. Generally, an effective amount of such compositions is added to water to form such aqueous washing and/or treatment solutions. The aqueous washing and/or treatment solution so formed is then contacted with the hair to be washed or treated therewith.

Without being bound by theory, it is believed the treatment of the hair with compositions disclosed in the present specification may decrease the dry-time of the hair after treatment. For example if the treatment were a hair-conditioning treatment applied in the shower, the time required for the hair to dry after such treatment would be reduced by virtue of the treatment, relative to the time required for the hair to dry if there had been no such treatment. Table 2 shows a decrease in the dry-time of hair as a result of treatment with examples of compositions disclosed in the present specification.

There is also provided a method of treating a surface comprising the step of applying the amino silicone nanoemulsion treatment composition of the present disclosure to a surface, where the surface is hair or skin and where the dry time relative to the untreated hair or skin is decreased, as measured by an decrease in Technical Dry Time. The Technical Dry Time may be less than about 3 seconds.

Hard Surfaces

The treatment compositions disclosed in the present specification may be used to clean or treat hard surfaces, such as those described herein. Typically at least a portion of the hard surface is contacted with an embodiment of the aforementioned hard surface care compositions, in neat form or diluted in a liquor, for example, a wash liquor and then the hard surface may be optionally washed and/or rinsed and/or dried without further treatment. A hard surface may be optionally washed and/or rinsed, contacted with an embodiment of the aforementioned hard surface care compositions and then optionally washed and/or rinsed and/or dried without further treatment. For purposes of the present disclosure, washing includes but is not limited to, scrubbing, and mechanical agitation.

The hard surface care compositions disclosed in the present specification can be used to form aqueous washing or treatment solutions for use in the washing and/or treatment of hard surfaces. Generally, an effective amount of such compositions is added to water to form such aqueous washing and/or treatment solutions. The aqueous washing and/or treatment solution so formed is then contacted with the hard surface to be washed or treated therewith.

Without being bound by theory, it is believed the treatment of the hard surface with compositions disclosed in the present specification may increase the contact angle of water or water-based composition and/or oily substances on the hard surface. Without being bound by theory it is believed that increasing the contact angle of substances on a hard surface increases the ease of removing said substances from the surface. Table 3 shows an increase in the contact angle of a silica wafer as a result of treatment with examples of compositions disclosed in the present specification.

There is also provided a method of treating a surface comprising the step of applying the amino silicone nanoemulsion treatment composition of the present disclosure to a surface, where the surface is a hard surface and where the contact angle relative to the untreated hard surface is increased. The contact angle may be greater than about 36 degrees.

While various specific embodiments have been described in detail herein, the present disclosure is intended to cover various different combinations of the disclosed embodiments and is not limited to those specific embodiments described herein. The various embodiments of the present disclosure may be better understood, when read in conjunction with the following representative examples. The following representative examples are included for purposes of illustration and not limitation.

EXAMPLES

For the sake of brevity, the present invention will be shown and described herein primarily by way of reference to obtaining the emulsion from a single reactor and dividing the obtained emulsion into multiple portions, however, it will be recognized that such teachings are intended to encompass and are equally applicable to obtaining the first, second, or multiple portions from a plurality of reactors or a plurality of emulsion batches obtained from a single reactor.

Nanoemulsion Preparations

1) Preparation of Amino Silicone Emulsions with Non-Resin Crosslinker

In a 36 oz jar, 102.0 g of amino silicone fluid (Mn=34527 g/mol, pendent group —$(CH_2)_3NH(CH_2)_2NH_2$ [corresponds to A], m/n=49, 71 mol % $SiMe_3$ end groups, 29 mol % SiOH/SiOMe end groups, obtainable from Shin-Etsu Silicones of America, Inc) are premixed with 12.0 g of Diethylene glycol monohexyl ether (obtainable from Sigma-Aldrich Chemie GmbH) using IKA RW20 Digital Dual-Range Mixer at 500 rpm for 30 minutes in a 50° C. oil bath. 8.4 g of Tergitol 15-s-5 and 12.0 g of Tergitol 15-s-12 (obtainable from Sigma-Aldrich Chemie GmbH) are added to the jar and mixed at 500 rpm at room temperature for 20 minutes. 463.8 g of DI water are added to the jar in two steps (309.2 g of DI water is added in the first step and 154.6 g of DI water is added in the second step) and mixed at 500 rpm at room temperature for total of 40 minutes. 1.74 ml of glacial acetic acid (obtainable from VWR International) are added to adjust pH to about 5.5. About 600 g of a 17% amino silicone nanoemulsions are prepared. The average particle size is 35 nm. 29.4 g of the nanoemulsions that contain 5 g of amino silicone are added to each individual reactor. The amount of the crosslinkers specified in the table below is then added to the reactor. The reactors are sealed and mixed for 16 hours at room temperature (20° C.-25° C.). After 16 hours of mixing the reactors are heated to 50° C. and held at 50° C. for an additional 25 hours.

Alternatively, as stated above, rather than dividing a single emulsion batch into multiple portions, the multiple portions may be obtained from separate reactors or separate emulsion batches from the same reactor.

TABLE 1

| Emulsions | Amino Silicone (grams) | Crosslinker (grams) | Crosslinker | Molar Ratio of Crosslinker/ Amino Silicone |
|---|---|---|---|---|
| 1 | 5 | 0 | 0 | 0 |
| 2 | 5 | 0.186 | DBH | 0.5 |
| 3 | 5 | 0.371 | DBH | 1 |
| 4 | 5 | 0.650 | DBH | 1.75 |
| 5 | 5 | 1.114 | DBH | 3 |
| 6 | 5 | 0.030 | DVA | 1 |
| 7 | 5 | 0.045 | DVA | 1.5 |
| 8 | 5 | 0.090 | DVA | 3 |
| 9 | 5 | 0.031 | BDDE | 1 |
| 10 | 5 | 0.077 | BDDE | 2.5 |

TABLE 1-continued

| Emulsions | Amino Silicone (grams) | Crosslinker (grams) | Crosslinker | Molar Ratio of Crosslinker/ Amino Silicone |
|---|---|---|---|---|
| 11* | 5 | 0.026 | DMA | 1 |
| 12* | 5 | 0.066 | DMA | 2.5 |
| 13 | 5 | 0.026 | HDDA | 0.75 |
| 14 | 5 | 0.034 | HDDA | 1 |
| 15 | 5 | 0.086 | HDDA | 2.5 |
| 16** | 5 | 0.0190 | DCB | 1 |
| 17** | 5 | 0.0475 | DCB | 2.5 |

*Added Hydrochloric Acid 10% greater than the amount of amines being reacted for the crosslinking.
**The emulsion was further heated at 85° C. for 72 hours.
Dibromohexane (DBH), 1,4-dichloro-2-butene (DCB), butanediol diepoxide (BDDE), dimethyl adipate (DMA), hexane diol diacrylate (HDDA) (all available from Sigma-Aldrich, Milwaukee, WI). Di-Vinyl Adipate (DVA) (available from Polysciences, Inc., Warrington, PA).

2) Preparation of Amino Silicone Emulsions with Non-Resin Crosslinker

In each individual reactor, 5 g of the same amino silicone fluid used in example 1 is premixed with 0.6 g of Diethylene glycol monohexyl ether using IKA RW20 Digital Dual-Range Mixer at 500 rpm for 30 minutes in a 50° C. oil bath. 0.4 g of Tergitol 15-s-5 and 0.6 g of Tergitol 15-s-12 are added to the reactor and mixed at 500 rpm at room temperature for 20 minutes. 22.7 g of DI water are added to the reactor in two steps (15.1 g of DI water is added in the first step and 7.6 g of DI water is added in the second step) and mixed at 500 rpm at room temperature for total of 40 minutes. The amount of the crosslinkers specified in the table below is then added to the reactor. The reactors are sealed and mixed for 16 hours at room temperature (20° C.-25° C.). After 16 hours of mixing the reactors are heated to 50° C. and held at 50° C. for an additional 25 hours. 1.74 ml of glacial acetic acid are added to adjust pH to about 5.5. About 29.4 g of a 17% amino silicone nanoemulsions are prepared. The average particle size is 60 to 250 nm.

TABLE 2

| Emulsions | Amino Silicone (grams) | Crosslinker (grams) | Crosslinker | Molar Ratio of Crosslinker/ Amino Silicone |
|---|---|---|---|---|
| 18 | 5 | 0.186 | DBH | 0.5 |
| 19 | 5 | 0.371 | DBH | 1 |
| 20 | 5 | 0.650 | DBH | 1.75 |
| 21 | 5 | 1.114 | DBH | 3 |
| 22 | 5 | 0.030 | DVA | 1 |
| 23 | 5 | 0.045 | DVA | 1.5 |
| 24 | 5 | 0.090 | DVA | 3 |
| 25 | 5 | 0.031 | BDDE | 1 |
| 26 | 5 | 0.077 | BDDE | 2.5 |
| 27* | 5 | 0.026 | DMA | 1 |
| 28* | 5 | 0.066 | DMA | 2.5 |
| 29 | 5 | 0.026 | HDDA | 0.75 |
| 30 | 5 | 0.034 | HDDA | 1 |
| 31 | 5 | 0.086 | HDDA | 2.5 |
| 32** | 5 | 0.0190 | DCB | 1 |
| 33** | 5 | 0.0475 | DCB | 2.5 |

*Added Hydrochloric Acid 10% greater than the amount of amines being reacted for the crosslinking.
**The emulsion was further heated at 85° C. for 72 hours.
Dibromohexane (DBH), 1,4-dichloro-2-butene (DCB), butanediol diepoxide (BDDE), dimethyl adipate (DMA), hexane diol diacrylate (HDDA) (all available from Sigma-Aldrich, Milwaukee, WI). Di-Vinyl Adipate (DVA) (available from Polysciences, Inc., Warrington, PA).

3) Preparation of Amino Silicone Emulsions with Non-Resin Crosslinker

In a 6 oz jar, 17.0 g of amino silicone fluid (Mn=34527 g/mol, pendent group —$(CH_2)_3NH(CH_2)_2NH_2$ [corresponds to A], m/n=49, 71 mol % $SiMe_3$ end groups, 29 mol % SiOH/SiOMe end groups, obtainable from Shin-Etsu Silicones of America, Inc) are premixed with 0.8 g of Di-Ethylene Glycol monoHexyl Ether (DEGHE, obtainable from Sigma-Aldrich Chemie GmbH) using IKA RW20 Digital Dual-Range Mixer at 500 rpm for 30 minutes in a 50° C. oil bath. 3.4 g of DiMethyl Bis (2-Steroyl Oxyethyl) Ammonium Chloride (DMBSOAC) (available from Evonik Degussa Corporation, Parsippany, N.J., US) are added to the jar and mixed at 500 rpm at room temperature for 20 minutes. 78.5 g of De-Ionized (DI) water are added to the jar in two steps (52.3 g of DI water is added in the first step and 26.2 g of DI water is added in the second step) and mixed at 500 rpm at room temperature for total of 40 minutes. Glacial acetic acid (obtainable from VWR International) is added to adjust pH to 5.5. About 100 g of a 17% amino silicone nanoemulsion is prepared. The average particle size is 125 nm. 29.4 g of the nanoemulsions that contain 5 g of amino silicone are added to each individual reactor. The amount of the crosslinkers specified in the table below is then added to the reactor. The reactors are sealed and mixed for 16 hours at room temperature (20° C.-25° C.). After 16 hours of mixing the reactors are heated to 50° C. and held at 50° C. for an additional 25 hours.

TABLE 3

| Emulsions | Amino Silicone (grams) | Crosslinker (grams) | Crosslinker | Molar Ratio of Crosslinker/ Amino Silicone |
|---|---|---|---|---|
| 34 | 5 | 0 | 0 | 0 |
| 35 | 5 | 0.030 | DVA | 1 |
| 36 | 5 | 0.371 | DBH | 1 |

Di-Vinyl Adipate (DVA) (available from Polysciences, Inc., Warrington, PA).
Di-BromoHexane (DBH) (all available from Sigma-Aldrich, Milwaukee, WI).

4) The emulsions in Table 4 were prepared by combining emulsions without crosslinker, nil-crosslinker (A), and corresponding emulsions with crosslinker (B), chosen from the emulsions shown in Tables 1-3, at room temperature.

TABLE 4

| Emulsions | Emulsion A (nil-crosslinker) | Emulsion B (crosslinker) | Crosslinker | Weight Ratio of A/B |
|---|---|---|---|---|
| 37 | Emulsion 1 | Emulsion 6 | DVA | 12:1 |
| 38 | | | | 6:1 |
| 39 | | | | 3:1 |
| 41 | Emulsion 34 | Emulsion 36 | DBH | 6:1 |

Di-Vinyl Adipate (DVA) (available from Polysciences, Inc., Warrington, PA).
Di-BromoHexane (DBH) (all available from Sigma-Aldrich, Milwaukee, WI).

Application Examples

Fabric Care Application:

Each of the nanoemulsions in Table 5 and Table 6 is diluted to make a treatment composition, in which the concentration of aminosilicone is either 100 ppm or 50 ppm, using DI water. Cotton fabric CW120 (obtainable from Empirical Manufacturing Company, Cincinnati, Ohio) is dipped in the solution and then dried at 60° C. for an hour in an oven. The Time to Wick (T2W) is measured on the fabrics according to the T2W testing method. Results are summarized in Tables 5 and 6 below.

Hair Care Application:

Each of the nanoemulsions in Table 5 is diluted to make a treatment composition, in which the concentration of aminosilicone is 10,000 ppm, using DI water. Hair Switches (obtainable from International Hair Imports & Products, New York) are dipped in the solution and the drying time is measured on the hair switches according to the Hair Drying Time test method. Results are summarized in the Table 5 below.

Hard Surface Application:

Each of the nanoemulsions in Table 5 is diluted to make a treatment composition, in which the concentration of aminosilicone is 500 ppm, using DI water. Solutions are dropped on Silica Wafers (obtainable from Silicon Valley Microelectronic, Inc, CA) then dried at room temperature for 24 hours. Contact angles are measured on the silica wafers according to the contact angle test method. Results are summarized in the Table 5 below.

TABLE 5

|  |  | Emulsions |  |  |  |  |  |
|---|---|---|---|---|---|---|---|
|  |  | 1 | 6 | 37 | 38 | 39 | 40* |
| Particle Size (nm) |  | 40 | 40 | 40 | 40 | 40 |  |
| Water T2W (seconds) | 50 ppm | 390 | 1800 | 2000 | 2600 | 1800 |  |
|  | 100 ppm | 3100 | >3600 | >3600 | >3600 | >3600 |  |
| Oil T2W (seconds) | 100 ppm | 17 | 20 | 20 | 19 | 19 |  |
| Drying Time (minutes) | 10,000 ppm | 2.7 | 2.2 | 2.2 | 2.2 | 2.2 | 3.5 |
| Contact *** Angle (°) | 500 ppm | 93 | 97 | 97 | 97 | 96 |  |

*Herbal Essences Drama Clean Shampoo (Lot#: 11225395LF).
**Contact Angle on non coated Silica wafer was 36°.

TABLE 6

|  |  | Emulsions |  |  |
|---|---|---|---|---|
|  |  | 34 | 36 | 41 |
| Water T2W (seconds) | 50 ppm | 200 | 50 | 350 |
|  | 100 ppm | 740 | 1130 | 2430 |
| Particle Size (nm) |  | 125 | 150 | 135 |
| pH |  | 5.5 | 5.5 | 5.5 |

Examples of Treatment and Cleaning Compositions

Liquid laundry additive compositions 1-3 shown below have detailed percentages based on 100% active basis.

TABLE 7

| Ingredient | 1 | 2 | 3 |
|---|---|---|---|
| Dosage | 30 g | 30 g | 30 g |
| emulsions 37-41 | 6.00% | 6.00% | 12.00% |
| cationic starch[1] | 1.20% | 1.20% | 1.20% |
| TAE80[2] | 0.25% | 0.25% | 0.25% |
| Antimicrobial[3] | 0.02% | 0.02% | 0.02% |
| Perfume | 0.40% | 0.40% | 0.40% |
| Butyl Carbitol | 3.00% | 3.00% | 2.00% |
| Polyamine N-oxide | 0.00% | 0.83% | 3.34% |

[1]Akzo, EXP 5617-2301-28, available from Akzo Nobel.
[2]Tallow alkyl ethoxylated alcohol having an average degree of ethoxylation of 80.
[3]Proxel GXL.

Examples 4-8 are formulations for a heavy duty liquid (HDL) laundry detergent prepared using the amino silicone nanoemulsion according to the present disclosure. The amino silicone nanoemulsion is added to the formulations in an amount ranging from 0.001% to 15.0% by weight.

TABLE 8

| Ingredient | 4 | 5 | 6 | 7 | 8 |
|---|---|---|---|---|---|
| emulsions 37-41 | 0.5 | 1.0 | 2.0 | 1.0 | 1.0 |
| Sodium alkyl ether sulfate | 20.5 | 20.5 | 20.5 |  |  |
| C12-15 Alkyl Polyethoxylate (1.1) Sulfonic Acid |  |  |  | 9.0 |  |

TABLE 8-continued

| Ingredient | 4 | 5 | 6 | 7 | 8 |
|---|---|---|---|---|---|
| Branched alcohol sulfate | 5.8 | 5.8 | 5.8 | | |
| Linear alkylbenzene sulfonic acid | 2.5 | 2.5 | 2.5 | 1.0 | 8.0 |
| Alkyl ethoxylate | 0.8 | 0.8 | 0.8 | 1.5 | 6.0 |
| Amine oxide | 0 | 0.5 | 2 | | 1.0 |
| Citric acid | 3.5 | 3.5 | 3.5 | 2.0 | 2.5 |
| Fatty acid | 2.0 | 2.0 | 2.0 | | 5.5 |
| Protease | 0.7 | 0.7 | 0.7 | 0.4 | 0.4 |
| Amylase | 0.37 | 0.37 | 0.37 | 0.08 | 0.08 |
| Mannanase | | | | 0.03 | 0.03 |
| Borax (38%) | 3.0 | 3.0 | 3.0 | 1.0 | |
| MEA Borate | | | | | 1.5 |
| Calcium and sodium formate | 0.22 | 0.22 | 0.22 | 0.7 | |
| Amine ethoxylate polymers | 1.2 | 0.5 | 1.0 | 1.0 | 1.5 |
| Zwitterionic amine ethoxylate polymer | 1.0 | 2.0 | 1.0 | | |
| DTPA[1] | 0.25 | 0.25 | 0.25 | 0.3 | 0.3 |
| Fluorescent whitening agent | 0.2 | 0.2 | 0.2 | | |
| Ethanol | 2.9 | 2.9 | 2.9 | 1.5 | 1.5 |
| Propylene Glycol | | | | 3.0 | 5.0 |
| Propanediol | 5.0 | 5.0 | 5.0 | | |
| Diethylene glycol | 2.56 | 2.56 | 2.56 | | |
| Polyethylene glycol 4000 | 0.11 | 0.11 | 0.11 | | |
| Monoethanolamine | 2.7 | 2.7 | 2.7 | 1.0 | 0.5 |
| Sodium hydroxide (50%) | 3.67 | 3.67 | 3.67 | 1.4 | 1.4 |
| Sodium cumene sulfonate | 0 | 0.5 | 1 | | 0.7 |
| Silicone suds suppressor | 0.01 | 0.01 | 0.01 | | 0.02 |
| Perfume | 0.5 | 0.5 | 0.5 | 0.30 | 0.3 |
| Dye | 0.01 | 0.01 | 0.01 | 0.016 | 0.016 |
| Opacifier[2] | 0.01 | 0.01 | 0.01 | | |
| Water | balance | balance | balance | balance | balance |
| | 100.0% | 100.0% | 100.0% | 100.0% | 100.0% |

[1]Diethylenetriaminepentaacetic acid, sodium salt
[2]Acusol OP 301.

Examples 9-12 are formulations for powder (granular) laundry detergents prepared using the amino silicone nanoemulsions according to the present disclosure. The amino silicone nanoemulsion is added to the formulations in an amount ranging from about 0.001% to about 15.0% by weight.

TABLE 9

| Ingredients | 9 | 10 | 11 | 12 |
|---|---|---|---|---|
| emulsions 37-41 | 0.5 | 2.5 | 5.0 | 10 |
| Sodium alkylbenzenesulfonate | 16.0000 | 14.0000 | 12.0000 | 7.9 |
| Sodium alkyl alcohol ethoxylate (3) sulfate | — | — | — | 4.73 |
| Sodium mid-cut alkyl sulfate | | 1.5000 | 1.5000 | — |
| Alkyl dimethyl hydroxyethyl quaternary amine (chloride) | — | — | — | 0.5 |
| Alkyl ethoxylate | 1.3000 | 1.3000 | 1.3000 | — |
| Polyamine[1] | — | — | — | 0.79 |
| Nonionic Polymer[2] | 1.0000 | 1.0000 | 1.0000 | 1.0 |
| Carboxymethylcellulose | 0.2000 | 0.2000 | 0.2000 | 1.0 |
| Sodium polyacrylate | — | — | — | |
| Sodium polyacrylate/maleate polymer | 0.7000 | 0.7000 | 0.7000 | 3.5 |
| Sodium tripolyphosphate | 10.0000 | 5.0000 | — | — |
| Zeolite | 16.0000 | 16.0000 | 16.0000 | |
| Citric Acid | — | — | — | 5.0 |
| Sodium Carbonate | 12.5000 | 12.5000 | 12.5000 | 25.0 |
| Sodium Silicate | 4.0 | 4.0 | 4.0 | — |
| Enzymes[3] | 0.30 | 0.30 | 0.30 | 0.5 |
| Minors including moisture[4] | Balance | balance | balance | balance |

[1]Hexamethylenediamine ethoxylated to 24 units for each hydrogen atom bonded to a nitrogen, quaternized.
[2]Comb polymer of polyethylene glycol and polyvinylacetate
[3]Enzyme cocktail selected from known detergent enzymes including amylase, cellulase, protease, and lipase.
[4]Balance to 100% can, for example, include minors like optical brightener, perfume, suds suppresser, soil dispersant, soil release polymer, chelating agents, bleach additives and boosters, dye transfer inhibiting agents, aesthetic enhancers (example: Speckles), additional water, and fillers, including sulfate, CaCO$_3$, talc, silicates, etc.

Example 13 is an automatic dishwasher powder detergent formulation and example 14 is an automatic dishwasher gel detergent formulation, both prepared using the amino silicone nanoemulsions according to the present disclosure. The amino silicone nanoemulsion is added to the formulations in an amount ranging from 0.001% to 15.0% by weight.

TABLE 10

| Ingredients | 13 | 14 |
|---|---|---|
| emulsions 37-41 | 10 | 15 |
| Polymer dispersant[1] | 5 | 3 |
| Carbonate | 35-40 | 0 |
| Sodium tripolyphosphate | 0-10 | 0-25 |
| Silicate solids | 6 | 0-10 |
| Bleach and Bleach activators | 4 | 2-6 |
| Enzymes | 0.3-0.6 | 0-1 |
| Disodium citrate dehydrate | 2-20 | 0 |
| Nonionic surfactant[2] | 0 | 0-2 |
| Polygel DKP[3] | 0 | 1-2 |
| Hydrozincite | 0 | 0-0.3 |
| Zinc Sulfate | 0 | 0-0.8 |
| NaOH | 0 | 0-4 |
| KOH | 0 | 0-15 |
| Boric Acid | 0 | 0-4 |
| 1,2-propanediol | 0 | 0-1 |
| NaCl | 0 | 0-0.5 |
| Sodium Benzoate | 0 | 0.1-6 |
| Water, sulfate, perfume, dyes and other adjuncts | Balance to 100% | Balance to 100% |

[1]Anionic polymers, such as Acusol ®, Alcosperse ® and other modified polyacrylic acid polymers.
[2]Such as SLF-18 Polytergent from Olin Corporation.
[3]Polyacrylate thickener from, e.g., 3V Co.

Examples 15 and 16 are liquid hand dishwashing formulations prepared using the amino silicone nanoemulsions according to the present disclosure. The amino silicone nanoemulsion is added to the formulations in an amount ranging from 0.001% to 15.0% by weight.

TABLE 11

| Ingredients | 15 | 16 |
| --- | --- | --- |
| $C_{12-13}$ Natural AE0.6S | 27.0 | 24.0 |
| $C_{10-14}$ mid-branched Amine Oxide | — | 6.0 |
| $C_{12-14}$ Linear Amine Oxide | 6.0 | — |
| SAFOL ® 23 Amine Oxide | 1.0 | 1.0 |
| C11E9 Nonionic[1] | 2.0 | 2.0 |
| Ethanol | 4.5 | 4.5 |
| Sodium cumene sulfonate | 1.6 | 1.6 |
| Polypropylene glycol 2000 | 0.8 | 0.8 |
| NaCl | 0.8 | 0.8 |
| 1,3 BAC Diamine[2] | 0.5 | 0.5 |
| emulsions 37-41 | 0.5 | 10 |
| Water | Balance | Balance |

[1]$C_{11}$ alkyl ethoxylated surfactant containing 9 ethoxy groups.
[2]1,3 bis(methylamine)-cyclohexane.

Example 17 is a laundry unit dose formulation prepared using the amino silicone nanoemulsions according to the present disclosure. The amino silicone nanoemulsion is added to the formulations in an amount ranging from 0.001% to 15.0% by weight.

TABLE 12

| Ingredients | 17 |
| --- | --- |
| emulsions 37-41 | 0.5-15 |
| Glycerol (min 99) | 5.3 |
| 1,2-propanediol | 10.0 |
| Citric Acid | 0.5 |
| Monoethanolamine | 10.0 |
| Caustic soda | — |
| Dequest 2010 | 1.1 |
| Potassium sulfite | 0.2 |
| Nonionic Marlipal C24EO7 | 20.1 |
| HLAS | 24.6 |
| Optical brightener FWA49 | 0.2 |
| C12-15 Fatty acid | 16.4 |
| Polymer Lutensit Z96 | 2.9 |
| Polyethyleneimine ethoxylate PEI600 E20 | 1.1 |
| MgCl2 | 0.2 |
| Enzymes | ppm |

Examples 18-23 are formulations for hard surface cleaning detergents prepared using the amino silicone nanoemulsion according to the present disclosure. The amino silicone nanoemulsion is added to the formulations in an amount ranging from 0.001% to 15.0% by weight.

TABLE 13

|  | 18 | 19 | 20 | 21 | 22 | 23 |
| --- | --- | --- | --- | --- | --- | --- |
| emulsions 37-41 | 0.5 | 2.0 | 5.0 | 1.0 | 10.0 | 0.3 |
| C9/11 EO 8 | 6.0 | 7.0 |  |  | 6.0 | 6.0 |
| C9/11 EO 5 |  |  | 3.5 |  |  |  |
| C12/14 EO21 |  |  | 3.5 |  |  |  |
| C11 EO 5 |  |  |  | 7.0 |  |  |
| NaLAS[2] | 2.00 | 1.8 |  |  |  | 2.25 |
| NaPS[1] |  |  | 3.1 | 3.0 | 3.0 |  |
| C12-14AS |  |  |  |  |  |  |
| NaCS[3] |  |  |  |  |  |  |
| C12-14 AO[4] | 1.50 | 1.50 | 3.9 | 2.0 |  | 1.25 |
| C12-14 Betaine |  |  |  | 1.0 | 3.0 |  |
| Quaternized Alkoxylated PEI | 0.1 | 0.5 | 0.1 | 0.2 | 0.2 | 0.05 |
| HM-polyacrylate | 0.76 | 0.75 |  |  |  | 0.65 |
| HM-HEC[5] |  |  |  | 0.6 | 0.8 |  |

TABLE 13-continued

|  | 18 | 19 | 20 | 21 | 22 | 23 |
| --- | --- | --- | --- | --- | --- | --- |
| X gum |  |  |  |  | 0.42 |  |
| $Na_2CO_3$ | 0.77 | 0.75 | 0.1 | 0.3 | 0.2 | 0.4 |
| Citric Acid | 0.046 | 0.3 | 0.75 | 0.75 | 0.3 | 0.3 |
| Caustic | Up to 0.46 | Up to 0.72 | Up to 0.5 | Up to 0.5 | Up to 0.3 | Up to 0.65 |
| Fatty Acid | 0.40 | 1.0 | 0.20 | 0.50 | 0.50 | 0.40 |
| Isofol ® 12[6] |  | 0.1 | 0.2 | 0.3 | 0.5 |  |
| Isofol ® 16[7] |  |  |  |  |  |  |
| DTPMP |  | 0.30 |  |  | 0.2 |  |
| DTPA | 0.25 |  |  |  |  | 0.25 |
| GLDA |  |  |  |  |  |  |
| IPA[9] |  |  |  | 2.0 |  |  |
| n-BPP[10] |  |  |  | 2.0 |  |  |
| n-BP[8] |  |  | 4.0 | 2.0 |  | 2.0 |
| Minors and Water | up to 100% | up to 100% | up to 100% | up to 100% | up to 100% | up to 100% |

[1]NaPS is sodium paraffin sulphonate, commercially available from Huls or Hoechst.
[2]NaLAS is sodium linear alkylbenzene sulphonate commercially available from A&W.
[3]NaCS is Sodium Cumene sulphonate commercially available from A&W.
[4]$C_{12-14}$ AO is a $C_{12-14}$ amine oxide surfactant.
[5]HM-HEC is a cetylhydroxyethylcellulose.
[6]Isofol 12 ® is 2-butyl octanol commercially available from Condea.
[7]Isofol 16 ® is 2-hexyl decanol commercially available from Condea.
[8]n-BP is normal butoxy propanol commercially available from Dow Chemicals.
[9]IPA is isopropanol.
[10]n-BPP is butoxy propoxy propanol available from Dow Chemicals.

Examples 24-27 are formulations for rinse-off personal care compositions, which are multi-phase body wash compositions comprising a cleansing phase, e.g., phase containing surfactant, and a benefit phase, e.g., a phase containing moisturizer. These compositions may be easily modified to contain a single, cleansing phase (for example, a single-phase, water-based composition generally comprising water, surfactant, perfume, and colorant), instead of cleansing and benefit phases. The following rinse-off personal care compositions may also be easily modified to contain antiperspirant actives. Water-based antiperspirant and deodorant compositions (e.g., roll-ons) are known. The amino silicone nanoemulsion according to the present disclosure is added to the formulations in an amount ranging from 0.001% to 15.0% by weight.

TABLE 14

| Ingredient | 24 | 25 |
| --- | --- | --- |
| Distilled Water | Q.S. | Q.S. |
| emulsions 37-41 | 0.001-15.0 | 0.001-15.0 |
| Sodium Tridecyl Ether Sulfate | 10.54 | 10.54 |
| Dehyton ML | 6.59 | 6.59 |
| Electrolyte | 4.01 | 4.01 |
| Iconol TDA3-Ethoxylated Tridecyl Alcohol | 0.84 | 0.84 |
| Cationic Polymer | 0.35 | 0.35 |
| Sodium Benzoate, NF | 0.24 | 0.24 |
| pH Adjustment Agent | 0.23 | 0.23 |
| Aqupec Ser W-300C | 0.17 | 0.17 |
| Dissovine na2-s | 0.13 | 0.13 |
| Kathon CG | 0.031 | 0.031 |
| Hydrogen peroxide solution, 20-40% | 0.004 | 0.004 |
| Soybean Oil | 15 | — |
| Petrolatume | — | 13 |
| Glyceryl monooleate | — | 2 |
| Mercaptopyridine-N-oxide (ZPT) | — | — |

TABLE 15

| Ingredient | 26 | 27 |
| --- | --- | --- |
| Water | Q.S. | Q.S. |
| emulsions 37-41 | 0.001-15.0 | 0.001-15.0 |

TABLE 15-continued

| Ingredient | 26 | 27 |
|---|---|---|
| Guar Hydroxy Propyl Trimonium Chloride | 0.2 | — |
| AM:TRIQUAT Copolymer | 0.2 | 0.2 |
| Sodium Laureth Sulfate, n = 1 | 10.5 | 6 |
| Sodium Lauryl Sulfate | — | 7 |
| Cocoamdopropyl Betaine | 1 | 1 |
| Ethylene Glycol Disterate | 2 | 2 |
| 330M silicone | 1.1 | — |
| Aminosilicone | — | 1.4 |
| Sodium Chloride | Up to 1.5% | Up to 1.5% |
| Fragrance | 0.75 | 0.75 |
| Preservatives, pH adjusters | Up to 1.3% | Up to 1.3% |
| Zinc Pyrithione | 1 | 1 |
| Zinc Hydroxy Carbonate | 1.61 | 1.61 |
| Petrolatum | 1 | 1 |
| Sodium Xylenesulfonate | Up to 1% | Up to 1% |

TABLE 16

Hair Shampoo Compositions

All ingredients in % as added

| Ingredient | 28 | 29 | 30 |
|---|---|---|---|
| Water | q.s. | q.s. | q.s. |
| emulsions 37-41 | 2 | 4 | 10 |
| Polyquaterium 76[1] | 0.25 | | 0.1 |
| Polquaterium 10[2] | | 0.25 | |
| Guar Hydroxypropyltrimonium Chloride[4] | | | 0.2 |
| Sodium Laureth Sulfate (SLE3S - 28% active)[5] | 21.43 | 35.71 | |
| Sodium Laureth Sulfate (SLE1S - 29% active)[6] | | | 37.93 |
| Sodium Lauryl Sulfate (SLS - 29% active)[7] | 12.07 | 24.14 | — |
| Coco monoethanolamide[8] | 1.0 | 0.5 | — |
| Cocoamdopropyl Betaine (30% active)[9] | 2.5 | — | 5.0 |
| Ethylene Glycol Disterate[10] | — | 1.5 | — |
| 330M silicone[11] | 1.43 | 1.43 | — |
| Silicone microemulsion[12] | — | — | 4 |
| Trihydroxystearin[13] | 0.25 | 0.25 | 0.25 |
| Sodium Chloride[14] | Adjust as needed for viscosity | Adjust as needed for viscosity | Adjust as needed for viscosity |
| Fragrance | 0.7 | 0.7 | 0.7 |
| Preservatives, pH adjusters | Up to 1% | Up to 1% | Up to 1% |

[1]Acrylamide:Triquat cationic polymer, tradname: Mirapol AT from Rhodia,
[2]KG30M cationic cellulose polymer from Amerchol Dow
[3]PolyDADMAC, tradename: Mirapol 100S from Rhodia
[4]Jaguar C500 from Rhodia
[5]Sodium Laureth (3 molar ethylene oxide) Sulfate at 28% active, supplier: P&G
[6]Sodium Laureth (1 molar ethylene oxide) sulfate at 29% active, supplier: P&G
[7]Sodium Lauryl Sulfate at 29% active, supplier: P&G
[8]Coco monethanolamide at 85% active, supplier: Stephan Co
[9]Tegobetaine F-B, 30% active, supplier: Goldschmidt Chemical
[10]Ethylene Glycol Disterate at 100% active, supplier: Goldschmidt Chemical
[11]330 M silicone, 100% active, supplier: Momentive (silicone used by P&G to make a 70% active, 30 um emulsion)
[12]Belsil 3560 VP silicone microemulsion from Wacker, 60,000 cst internal viscosity of silicone, approx. 125 nm
[13]Thixin R from Rheox Inc.
[14]Sodium Chloride USP (food grade) from Morton

TABLE 17

Hair Gel Products

| Ingredient | 31 | 32 | 33 | 34 | 35 |
|---|---|---|---|---|---|
| emulsions 37-41 | 2.00 g | 1.00 g | 1.00 g | 3.80 g | 3.80 g |
| Luviset ® Clear | 1.00 g | 1.50 g | 3.00 g | 1.00 g | 1.50 g |
| Luviskol ® VA 64 | | 3.00 g | | | |
| Surfactant 193 | 1.50 g | | 1.50 g | | |
| Carbomer | 0.30 g | | | | |
| AMP 95% | 0.30 g | | 0.26 g | 0.30 g | 0.26 g |
| Emulgin L | 0.20 g | | | | |
| Perfume | 0.15 g | 0.20 g | 0.30 g | 0.20 g | 0.20 g |
| Natrosol ® G | 0.40 g | | | | |
| Ethanol | 16.50 g | 18.00 g | 34.20 g | 5.00 g | 4.50 g |
| Aminomethylpropanol 95% aqueous solution | | 0.10 g | | | |
| Pemulen ® | | | 0.35 g | | |
| PEG-40 Hydrogenated Castor Oil | | 0.20 g | | 0.20 g | |
| Aculyn ® 48 | | 0.50 g | | | |
| Aquaflex ® SF 40 | 2.80 g | | 2.80 g | | |
| Methylmethoxycinnamate | | | 0.30 g | | |
| VA/CROTONATES COPOLYMER (Luviset ® CA 66) | | | | 2.50 g | |
| Sorbitol | | | | 4.20 g | |
| Direct dye | | | | 1.00 g | |
| Carbomer (Tego Carbomer) | | | | 0.80 g | |
| Methylparaben | | | | 0.20 g | 0.20 g |
| Panthenol | | | | 0.10 g | |
| Glycerol | | | | | 5.20 g |
| Propylene glycol | | | | | 4.00 g |
| Ammonium Acryloyldimethyltaurate/VP Copolymer (Aristoflex ® AVC) | | | | | 0.35 g |
| Polysorbate-40 | | | | | 1.00 g |
| PEG-25 PABA | | | | | 0.50 |
| Water | Balance | Balance | Balance | Balance | Balance |

TABLE 18

Pump Hair Foams

| Ingredient | 36 | 37 | 38 | 39 |
|---|---|---|---|---|
| emulsions 37-41 | 0.20 g | 2.20 g | 1.20 g | 1.20 g |
| Luviset ® Clear | 1.30 g | 2.00 g | 1.30 g | 1.80 g |
| Vinyl acetate/crotonic acid copolymer | 0.30 g | | | |
| Cocamidopropyl Hydroxysultaine | 0.40 g | 0.20 g | 0.40 g | 0.40 g |
| Citric acid | 0.10 g | 0.10 g | | |
| Ethanol | 8.90 g | 8.90 g | | 8.90 g |
| Betaine | 0.10 g | 0.10 g | | |
| Perfume Ingredient | 0.15 g | 0.15 g | 0.15 g | 0.15 g |
| Celquat ® L200 | | 0.30 g | | |
| Direct dye | | 0.80 g | 0.20 g | 1.90 g |
| Cetyltrimethylammonium chloride | | 0.20 g | | |
| Polyquaternium-11 | | | 0.30 g | |
| Propylene glycol | | | 1.00 g | |
| Methylparaben | | | 0.20 g | |
| Rosemary leaf extract (Extrapon ® Rosemary) | | | | 0.10 g |
| Extrapon ® seven herbs - extract | | | | 0.10 g |
| Panthenyl ethyl ether | | | | 0.10 g |
| Water | Balance | Balance | Balance | Balance |

TABLE 19

Aerosol and Non-Aerosol Hair Products

| Ingredient | 40 | 41 | 42 | 43 | 44 | 45 | 46 |
|---|---|---|---|---|---|---|---|
| emulsions 37-41 | 4.20 g | 5.20 g | 3.20 g | 1.20 g | 0.20 g | 1.20 g | 2.20 g |
| Luviset ® Clear | 1.50 g | 1.50 g | 2.10 g | 2.10 g | 1.50 g | 2.50 g | 1.00 g |
| Butyl monoester of methyl vinyl ether/maleic acid copolymer | 0.50 g | | | | | | |
| Butane | 4.00 g | 4.00 g | 4.00 g | 4.00 g | | | |
| Propane | 4.00 g | 4.00 g | 4.00 g | 4.00 g | | | |
| Ethanol | 8.90 g | | | 8.90 g | 2.70 g | 28.50 g | 28.50 g |
| PEG-25 PABA | 0.40 g | | | 0.40 g | 0.70 g | | |
| Betaine | 0.15 g | 0.15 g | | | | | |
| Perfume | 0.15 g | 0.15 g | 0.20 g | 0.20 g | 0.25 g | 0.25 g | |
| Laureth-4 | 0.20 g | 0.20 g | | 0.20 g | | | |
| Cetrimonium bromide | 0.05 g | | | | | | |
| Amodimethicone | 0.50 g | | | | | | |
| Polyquaternium-47 | | 0.50 g | 1.00 g | 0.50 g | | | |
| Dow Corning 1401 | | 0.25 g | | | | | |
| 2-Ethylhexyl 4-methoxycinnamate | | 0.20 g | | | | | |
| Cetrimonium chloride | | 0.07 g | 0.07 g | | 0.20 g | | |
| Copolymer 845 | | | 2.50 g | | | | |
| Panthenol | | | 0.20 g | 0.20 g | 0.35 g | | |
| Abilquat ® 3270 | | | 0.70 g | | | | |
| Vinyl acetate/crotonic acid copolymer | | | | 0.60 g | | | |
| C9-C11 Pareth-8 | | | | 0.07 g | | | |
| Aquaflex ® FX-64 | | | | | 1.00 g | | |
| Polyquaternium-35 | | | | | 1.00 g | | |
| PEG-40 Hydrogenated Castor Oil | | | | | 0.21 g | | |
| Octylacrylamide/Acrylates/Butylaminoethyl-methacrylate Copolymer (Amphomer ®) | | | | | | 2.00 g | 0.65 g |
| Aminomethylpropanol 95% | | | | | | 0.60 g | 0.60 g |
| Celquat ® L200 | | | | | | | 0.20 g |
| Cetyltrimethylammonium chloride | | | | | | | 0.20 g |
| Water | Balance | Balance | Balance | Balance | Balance | Balance | Balance |

TABLE 20

Rinse Out Conditioner

| Ingredient | 47 |
|---|---|
| emulsions 37-41 | 3.00 g |
| cetyltrimethyl ammonium chloride | 1.00 g |
| polymethylphenyl siloxane (CTFA: OUATERNIUM-80; Abil Quat ® 3272) | 1.00 g |
| phenoxy ethanol | 0.40 g |
| PHB-methylester | 0.20 g |
| Copolymer of aminoethyl aminopropyl siloxane and dimethyl siloxane emulsion as a mixture with polyethylenglycol ether of tridecyl alcohol and cetyl trimethyl ammoniumchloride (CTFA: AMODIMETHICONE & TRIDECETH-12 & CETRIMONIUM CHLORIDE; Dow Corning 949 Cationic Emulsion ®) | 1.00 g |
| Isododecane | 5.00 g |
| perfume oil | 0.40 g |
| Water | Balance |

TABLE 21

Rinse Out Conditioner

| Ingredient | 48 |
|---|---|
| CETEARYL ALCOHOL | 4.50 g |
| CETRIMONIUM CHLORIDE (GENAMIN CTAC 50) | 1.30 g |
| Citric acid | 0.30 g |
| Perfume | 0.15 g |
| emulsions 37-41 | 6.00 g |
| Water | Balance |

TABLE 22

Leave In Conditioner

| Ingredient | 49 |
|---|---|
| emulsions 37-41 | 1.00 g |
| 2-hydroxy-3-(trimethylamonio)propylether chloride guar gum | 0.50 g |
| sodium benzoate | 0.50 g |
| glyoxylic acid | 0.10 g |
| Creatine | 0.20 g |
| behenyl trimethylammonium chloride | 0.80 g |
| cetylstearyl alcohol | 0.60 g |
| stearic acid polyethylenglycol (20 EO) | 0.10 g |
| hydrolyzed silk | 0.10 g |
| perfume oil | 0.20 g |
| Water | Balance |

TABLE 23

Leave In Conditioner

| Ingredient | 50 |
|---|---|
| emulsions 37-41 | 1.80 g |
| vitamine E-acetate | 0.10 g |
| polymethylphenyl siloxane (CTFA: OUATERNIUM-80; Abil Quat$^{(R)}$ 3272) | 0.50 g |
| propylene glycol | 10.00 g |
| behenyl trimethylammonium chloride | 0.50 g |
| sodium chloride | 0.05 g |
| d-panthenol | 0.30 g |
| PHB-propylester | 0.30 g |
| Isododecane | 2.00 g |
| perfume oil | 0.20 g |
| Water | Balance |

TABLE 24

Split Ends Fluid

| Ingredient | 51 |
|---|---|
| emulsions 37-41 | 3.50 g |
| vitamine E-acetate | 0.10 g |
| polymethylphenyl siloxane (CTFA: OUATERNIUM-80; Abil Quat$^{(R)}$ 3272) | 0.50 g |
| cyclo penta siloxane (CTFA: CYCLOMETHICONE) | 21.00 g |
| dihydroxy polydimethyl siloxane (CTFA: DIMETHICONOL) | 2.50 g |
| Ethanol | 1.50 g |
| perfume oil | 0.60 g |
| Water | Balance |

TABLE 25

Leave In Conditioner

| Ingredient | 52 |
|---|---|
| JAGUAR C-17 | 0.30 g |
| NATROSOL 250 HHR | 0.30 g |
| emulsions 37-41 | 20.00 g |
| Eumulgin L | 0.20 g |
| Perfume | 0.15 g |
| PHENOXYETHANOL | 0.20 g |
| PHB-METHYLESTER | 0.12 g |
| DISODIUM EDTA | 0.10 g |
| Water | Balance |

TABLE 26

Aerosol Styling mousse

| Ingredient | 53 |
|---|---|
| Polyquaternium-11 (GAFQUAT 755 N) | 15.00 g |
| emulsions 37-41 | 5.00 g |
| Laureth-4 | 0.40 g |
| Perfume | 0.15 g |
| PHENOXYETHANOL | 0.20 g |
| PHB-METHYLESTER | 0.12 g |
| DISODIUM EDTA | 0.10 g |
| Propane/Butane | 6.00 g |
| Water | Balance |

TABLE 27

Volumizing Aerosol Foam

| Ingredient | 54 |
|---|---|
| emulsions 37-41 | 1.20 g |
| Luviset ® Clear | 2.00 g |
| Chitosan | 0.27 g |
| Celquat ® L200 | 1.00 g |
| Pyrrolidone carboxylic acid | 0.23 g |
| Direct dye | 0.90 g |
| Laureth-4 | 0.20 g |
| Cetrimonium chloride | 0.10 g |
| Perfume, preservative | 0.50 g |
| Water | Balance |

The composition is bottled with propane/butane 4.8 bar in the ratio of active ingredient solution:propellant gas=94:6 in an aerosol can with foaming head. Through use of the product on the hair, the hairstyle is given long-lasting volume.

Test Methods

Time to Wick (T2W) Measurement Method

The fabric Time to Wick property is a measure of the water repellency or oil repellency of a fabric, where longer times indicate greater repellency. Water repellency is measured when a drop of water is applied to the fabric, whereas oil repellency is measured when a drop of oil is applied to the fabric. The Time to Wick value is measured as follows: The tests are conducted in a well-ventilated lab whose humidity is between 40 to 60% RH. and temperature is between 20 to 25° C. All samples are preconditioned for at least 24 hours in that lab prior to testing. Untreated control white cotton fabric is prepared from new, 100% cotton, woven, white bed sheets, which are de-sized by 3 rounds of laundering using the AATCC 2003 standard reference liquid detergent without optical brighteners (AATCC—American Association of Textile Chemists and Colorists, Research Triangle Park, N.C., USA), then cut to yield fabric pieces approximately 10 cm×10 cm in size. Treated test fabric is the same as the untreated control fabric plus the addition of the treatment being tested, which is applied to the fabric in accordance with the manufacturer's instructions, after the de-sizing steps.

On a flat, level hard surface (e.g. benchtop) is placed a fresh square of a paper towel at least 10 cm×10 cm in size, and on top of that is placed a square of the prepared fabric. A 300 μL drop of liquid is then dispensed onto the fabric surface from a calibrated pipettor. The drop is DI water when measuring water repellency or it is Canola Oil when measuring oil repellency. The process of absorption of the liquid drop is visually monitored using a video camera such as a Webcam Pro 9000 (Logitech, Silicon Valley, Calif., USA), integrated with a laptop computer, and displaying either an electronic timestamp or a stopwatch timer within the field of view, which counts the time elapsed in seconds. The imaging conditions are set up such that the margins of the drop and the fabric surface are both clearly visible and simultaneously in focus, with the viewing angle being from directly above. Nine drops are administered per fabric square, with each drop placed at a different location separate from all adjacent drops.

The recorded video is used to determine the time—at drop addition and the time—at drop absorption. For each drop, the time differential between those two time points is calculated and recorded. The time at drop addition is defined as being the earliest time point at which a portion of the drop is observed making contact with the surface of the fabric. The time at drop absorption is defined as being the earliest time point at which no portion of the drop is observed rising above the surface of the fabric. After 60 minutes, the video capture is terminated regardless of any remaining drops left unabsorbed. Such drops are recorded as having a time differential of 60 mins. The Time to Wick value for a given liquid on fabric is the average of the time differentials recorded for 9 drops of that liquid. In order to determine the effect of a treatment, comparisons are made between the average Time to Wick value obtained from the treated fabric, versus the average obtained from its untreated control fabric using the same liquid, where longer times indicate greater repellency.

Particle Size Measurement Test Method

Nanoemulsions were diluted with DI water to a concentration of 1% prior to making particle size measurements. The particle size measurements are made via dynamic light scattering on a model 3D-DLS spectrometer instrument (LS Instruments, Switzerland). The software accompanying the instrument (version 6.3, LS Instruments, Switzerland) is used to control the spectrometer to acquire data and conduct particle size analysis in dynamic light scattering mode. The instrument is set with the following conditions: Wavelength=632 nm (HeNe laser), scattering angle=90°, Temperature=297 Kelvin (measured by the instrument with sample placed in water bath and equilibrated for 10 minutes), Integration Time $T_{int}$=2 min, Count rate set between 100-250 kcps (attenuating the laser power), Lag time set between 0.7 microseconds to 50 seconds. All measurements were taken in autocorrelation mode. All data are reported as the second-order Cumulant fit to the autocorrelation function. The nanoemulsion's particle size is reported as the average diameter value measured, when calculated on a volume-weighted basis. A nanoemulsion whose particle size is less than 200 nm is defined as being a nanoemulsion.

Technical Drying Time Test Method

Switches of human hair, which are of straight low-lift medium brown Caucasian hair, approximately 20 cm long and having approximately 4 g of hair per switch, are obtained from International Hair Importers & Products (IHIP) (White Plains, N.Y., USA) for use in the Hair Drying Time Test. Use three switches of hair per treatment and per control. To prepare the hair, measure and record the initial dry weight of each hair switch, then wash each switch using the following shampoo and instructions. Hang the switches on a rod above a sink, and wet the hair with 38° C. DI water until saturated. Squeeze out excess water and apply the specified shampoo, at a dosage of 0.1 g shampoo per 1 g hair (dry wt). Apply half the total amount of shampoo on one side of the switch and rest on the other side. Massage the hair switches by hand for 60 seconds to create lather throughout the switch. Rinse thoroughly with 38° C. DI water running at 4 to 6 L/min for at least 2 minutes (1 min per side). Use hand manipulation to squeeze out the excess water. Up to 35 g of hair can be shampooed simultaneously. Each ingredient in the shampoo is listed below at its final concentration in percent by weight:

| Shampoo Ingredients | Wt % |
|---|---|
| Sodium Lauryl Sulfate | 5.0 |
| Sodium Laureth Sulfate | 10.0 |
| Cocamidopropyl betaine | 0.8 |
| Guar Cationic Polymer | 0.5 |
| Extracts of *Camellia Sinensis* Leaf, Citrus *Auranfium Dulcis* Flower, *Zea Mays* Silk. | 2.1 |
| Sodium Citrate | 0.4 |
| Sodium EDTA | 0.16 |
| Citric Acid | 0.04 |
| Sodium Benzoate | 0.25 |
| DI Water to balance to 100% | |

The remaining steps in the hair dying time test method are conducted in an air conditioned room having a temperature of 20 to 25° C., and a relative humidity of 40 to 60% RH, and are conducted in immediate succession without any delays or pauses between steps. Apply the treatment product being tested onto just one hair switch at a time, using switches prepared and shampooed as specified above. Prior to applying the treatment, ensure that the hair switch is thoroughly saturated with 38° C. DI water but is not dripping. Place the switch in a plastic weighing-boat dish approximately 13 cm×13 cm, and dose the wet hair with 1 g of the treatment solution being tested per 4 g of hair dry weight. Apply the treatment solution homogenously along the length of the hair. Massage the treatment solution into the hair switch in the dish for 3 minutes with hand manipulation, ensuring that all the hair fibers are exposed to the solution. The switch is then subjected to multiple cycles of blow drying and weighing, where the duration of blow drying and the subsequent switch weight are recorded for each cycle, and are compared to the switch's initial dry weight. Hang the hair switch vertically and commence blow drying while the hair is still thoroughly saturated with water and treatment solution. Blow dry the hair switch using a Sunbeam 1600 Watt hand-held electric hair dryer with diffuser nozzle adapter, with the heat level selection set on High, (Sunbeam Corporation Limited, Botany, Australia), and positioned 7 cm away from the hair. After 3 minutes of blow drying (1.5 mins per side), weigh the hair switch and record the weight. Press the hair switch gently between two kitchen paper towels for 2 seconds and reweigh. Repeatedly blow dry and reweigh the hair again using drying time increments of 30 seconds for each cycle. When the switch weight approaches its initial dry weight, reduce the drying time increments to 20 seconds for each subsequent cycle, and continue the drying and weighing cycles until the hair switch returns to its initial dry weight. The switch's total hair drying time is determined by summing all of the drying times that were required to return the hair to its initial dry weight. This cumulative value is the switch's Hair Drying Time. The hair drying times obtained from the three replicate switches in each treatment are averaged to determine the mean hair drying time for the treatment. To determine the effect of the treatment on hair drying time, the mean hair drying time for the treatment is compared to the mean hair drying time obtained from 3 control switches, which were each dosed with 1 g of DI water instead of 1 g of treatment solution.

The above Technical Dry Time Test Method is also relevant to skin.

Contact Angle Test Method

The static contact angle of a nanoemulsion is determined by measuring a sessile droplet of water placed on a nanoemulsion-coated surface, as measured via an optical profile image of the droplet. The surface is prepared using 2.5 cm×2.5 cm sized silica wafers (J#19777), as available from Silicon Valley Microelectronics Inc. (SVM), (Santa Clara, Calif., USA). Clean the wafers by rinsing with DI water followed by further rinses with ethanol and then with acetone, ensuring that both the organic solvents are of a high purity grade such as that suitable for use in LC-MS analyses. Expose the wafers to ozone for 15 minutes, by placing a cleaned wafer into a specimen chamber attached to an ozone generator such as the UV/Ozone Pro Cleaner™ (manufactured by Bioforce Nanoscience, Ames, Iowa, USA). The nanoemulsion to be tested is then spin-coated onto the cleaned and ozonated wafers. To achieve this coating, prepare the emulsion to be tested at a concentration of 500 ppm in DI water. Dispense 1600 µL of the nanoemulsion onto a silica wafer, wait 1 min then spin the wafer at 2000 rpm for 30 seconds in a spin coater instrument, such as the WS-400B-6NPP/Lite/AS2 (manufactured by Laurell Technology Corporation, North Wales, Pa., USA). The spin-coated wafer is the then allowed to cure for 24 hours at room temp or in an 80° C. oven for 1 hour. With the wafer at room temperature, use a contact angle goniometer such as the FTA 200 manufactured by First Ten Angstroms, Inc, Portsmouth, Va., USA), to measure the static contact angle of a sessile 10 µL drop of DI water placed onto the coated surface of the silica wafer. Prepare and measure 3 replicate spin-coated wafers for each nanoemulsion to be tested, and average the replicate contact angle results to obtain the contact angle for that nanoemulsion. The contact angle of the cleaned but uncoated silica wafer is 36°.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of making an amino silicone nanoemulsion comprising the steps of:

a) mixing one or more liquid amino silicone compounds represented by formula (1) below with a solvent to form a mixture of amino silicone and solvent:

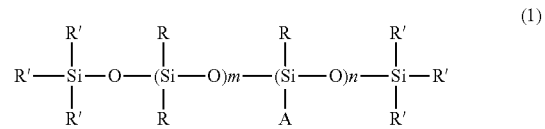

(1)

where each R is an alkyl group with 1-10 carbon atoms, wherein each R' is an alkyl group having 1-10 carbon atoms, a phenyl group, a monovalent group represented by formula (2) below, or a monovalent group represented by the formula: —$OR^3$, where $R^3$ is a hydrogen atom or a monovalent hydrocarbon group with 1-10 carbon atoms;

m is a whole number from 50 to 1000, n is a whole number from 1 to 100,

A is a monovalent group represented by formula (2) below:

—$R^1$—(NH—$R^2$)a-$NH_2$ (2)

where $R^1$ and $R^2$ are divalent hydrocarbon groups with 1-10 carbon atoms;

a is a whole number from 0 to 4;

b) mixing said mixture of amino silicone and solvent with surfactant, water, and, optionally, a protonating agent, to form a nanoemulsion;

c) dividing said nanoemulsion into a first nanoemulsion and a second nanoemulsion;

d) mixing said second nanoemulsion with a non-resin crosslinking agent, to form a third nanoemulsion, i. at a temperature ranging from about 20° C. to about 100° C.;

ii. wherein said non-resin crosslinking agent is represented by formula (3):

R-$L_n$ (3)

wherein n≥2, R is a polyvalent, saturated or unsaturated, substituted or unsubstituted, organic moiety comprising 2-30 carbon atoms, and each L, identical or different, is a functional group capable of reacting with an amino group;

iii. wherein a molar ratio of said non-resin crosslinking agent to said one or more liquid amino silicone compounds in said third nanoemulsion is from about 0.05:1 to about 10:1;

e) mixing said first nanoemulsion with said third nanoemulsion to form said amino silicone nanoemulsion.

2. The method of claim 1 wherein the molar ratio of said non-resin crosslinking agent to said one or more liquid amino silicone compounds in said third nanoemulsion is from about 0.1:1 to about 5:1.

3. The method of claim 1 wherein the molar ratio of said non-resin crosslinking agent to said one or more liquid amino silicone compounds in said third nanoemulsion is from about 0.5:1 to about 3:1.

4. The method of claim 1 further comprising the step of mixing said first nanoemulsion with a non-resin crosslinking agent to form a fifth nanoemulsion:
  i. at a temperature ranging from about 20° C. to about 100° C.;
  ii. wherein said non-resin crosslinking agent is represented by formula (3):

$$R\text{-}L_n \tag{3}$$

wherein n≥2, R is a polyvalent, saturated or unsaturated, substituted or unsubstituted, organic moiety comprising 2-30 carbon atoms, and each L, identical or different, is a functional group capable of reacting with an amino group;

iii. wherein the molar ratio of said non-resin crosslinking agent to said one or more liquid amino silicone compounds in said fifth nanoemulsion is from about 0.05:1 to about 10:1 wherein step e) comprises mixing said fifth nanoemulsion with said third nanoemulsion to form said amino silicone nanoemulsion.

5. The method of claim 4 wherein the molar ratio of said non-resin crosslinking agent to said one or more liquid amino silicone compounds in said fifth nanoemulsion is from about 0.1:1 to about 5:1.

6. The method of claim 4 wherein the molar ratio of said non-resin crosslinking agent to said one or more liquid amino silicone compounds in said fifth nanoemulsion is from about 0.5:1 to about 3:1.

7. The method of claim 4 wherein the molar ratio of said non-resin crosslinking agent to said one or more liquid amino silicone compounds in said fifth nanoemulsion is different from the molar ratio of said non-resin crosslinking agent to said one or more liquid amino silicone compounds in said third nanoemulsion.

8. The method according to claim 1 wherein said amino silicone nanoemulsion is substantially free of a silicone resin.

* * * * *